US007651998B1

(12) United States Patent
MacDonald et al.

(10) Patent No.: US 7,651,998 B1
(45) Date of Patent: Jan. 26, 2010

(54) ANTIBODY DEPENDENT ENHANCEMENT OF VENEZUELAN EQUINE ENCEPHALITIS VECTOR INFECTION

(75) Inventors: Gene H. MacDonald, Chapel Hill, NC (US); Robert E. Johnston, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 600 days.

(21) Appl. No.: 10/069,305

(22) PCT Filed: Aug. 30, 2000

(86) PCT No.: PCT/US00/23845

§ 371 (c)(1),
(2), (4) Date: Jun. 6, 2002

(87) PCT Pub. No.: WO01/16343

PCT Pub. Date: Mar. 8, 2001

Related U.S. Application Data

(60) Provisional application No. 60/151,718, filed on Aug. 31, 1999, provisional application No. 60/177,435, filed on Jan. 21, 2000.

(51) Int. Cl.
*A61K 31/70* (2006.01)
(52) U.S. Cl. ...................................................... 514/44
(58) Field of Classification Search .................... 514/44
See application file for complete search history.

(56) References Cited

U.S. PATENT DOCUMENTS

| 5,789,245 | A | * | 8/1998 | Dubensky et al. | ........ | 435/320.1 |
| 5,994,126 | A | | 11/1999 | Steinman et al. | ............ | 435/325 |
| 6,004,807 | A | | 12/1999 | Banchereau et al. | ........ | 435/325 |

FOREIGN PATENT DOCUMENTS

| EP | 0659885 A1 | | 12/1994 |
| WO | WO 9532733 | | 12/1995 |
| WO | WO 99/25858 | * | 5/1999 |
| WO | WO/01/47456 A1 | | 7/2001 |

OTHER PUBLICATIONS

Ohno, K. et al. Nature Biotechnology, 1997; vol. 15, pp. 763-767.*
Gould et al. (J. Gen. Virol., 1989; vol. 70, pp. 1605-1608).*
Linn et al., Antibody-dependent enhancement and persistence in macrophages of an arbovirus associated with arthritis, *Journal of General Virology*, 77, 407-411, (1996).
XP002157462, *CD Antigen designations*, http://wwwamb.casaccia.enea.it/glc/CD-table htm, (1995).
International Search Report Corresponding to PCT/US00/23845;May 2, 2001.
Berge et al., "Studies on the virus of venezuelan equine encephalomyelitis," *Journal of Immunology*, 87: 509-517 (1961).
Polo et al. "Molecular Analysis of Sindbis Virus Pathogensis in Neonatal Mice by Using Virus Recombinants Constructed In Vitro" *Journal of Virology* 62: 2124-2133 (1988).
Barrett, A.D.T. & E.A. Gould "Antibody-mediated Early Death in vivo after Infection with Yellow Fever Virus." *Journal of General Virology* 67:2530-2542 (1986).
Bowers, W.E. & E.M. Goodell "Dendritic cell ontogeny." *Research in Immunology* 140(9):880-883 (1989).
Chanas, A.C., et al. "Monoclonal Antibodies to Sindbis Virus Glycoprotein EI can Neutralize, Enhance Infectivity, and Independently Inhibit Haemagglutination or Haemolysis." *Journal of General Virology* 58:37-46 (1982).
Davis, Nancy L., et al. "Vaccination of Macaques against Pathogenic Simian Immunodeficiency Virus with Venezuelan Equine Encephalitis Virus Replicon Particles." *Journal of Virology* 74(1):371-378 (2000).
Flynn, Daniel C., et al. "Antibody-Mediated Activation of Sindbis Virus." *Virology* 166:82-90 (1988).
Füst, G. "Enhancing antibodies in HIV infection." *Parasitology* Supplemental 115:127-140 (1997).
Guyre, Paul M. et al. "Increased potency of Fc-receptor-targeted antigens." *Cancer Immunology, Immunotherapy* 45:146-148 (1997).
Hawkes, R.A. & K.J. Lafferty "The Enhancement of Virus Infectivity by Antibody." *Virology* 33:250-261 (1967).
Heufler, Christine, et al. "Granulocyte/Macrophage Colony-Stimulating Factor and Interleukin 1 Mediate the Maturation of Murine Epidermal Langerhans Cells into Potent Immunostimulatory Dentritic Cells." *Journal of Experimental Medicine* 167(February):700-705 (1988).
Inada, T. et al. "Enhancing Antibodies, Macrophages and Virulence in Mouse Cytomegalovirus Infection." *Journal of General Virology* 66:871-878 (1985).
Inada, T. & C.A. Mims "Association of Virulence of Murine Cytomegalovirus with Macrophage Susceptibility and with Virion-bound Non-neutralizing Antibody." *Journal of General Virology* 66:879-882 (1985).
MacDonald, Gene H. & Robert E. Johnston "Role of Dendritic Cell Targeting in Venezuelan Equine Encephalitis Virus Pathogenesis." *Journal of Virology* 74(2):914-922 (2000).
Mady, Brian J., et al. "Neuraminidase augments Fcγ receptor II-mediated antibody-dependent enhancement of dengue virus infection." *Journal of General Virology* 74:839-844 (1993).

(Continued)

*Primary Examiner*—J. E Angell
(74) *Attorney, Agent, or Firm*—Myers Bigel Sibley & Sajovec, P.A.

(57) ABSTRACT

The present invention provides compositions and methods for delivering a nucleotide sequence to a cell using an alphavirus vector that is complexed with an enhancing antibody that specifically binds to the alphavirus vector. Venezuelan Equine Encephalitis vectors are preferred. The cell may be a cell in vitro or in vivo. Alternatively, the cell may be removed from a subject, administered the alphavirus vector ex vivo and then administered to a subject. Antigen-presenting cells are preferred, with dendritic cells being more preferred. Also provided are methods of producing an immune response in a subject, e.g., for producing an immune response against an antigen associated with a pathogen or for immunotherapy of cancer of tumors.

9 Claims, 10 Drawing Sheets

OTHER PUBLICATIONS

McKenzie, Steven E. "Biological advances and clinical application of Fc receptors for IgG." *Current Opinion in Hematology* 1:45-52 (1994).

Morens, David M. & S.B. Halstead "Measurement antibody-dependent infection enhancement of four dengue virus serotypes by monoclonal and polyclonal antibodies." *Journal of General Virology* 71:2909-2914 (1990).

Morens, David M. "Antibody-Dependent Enhancement of Infection and the Pathogenesis of Viral Disease." *Clinical Infectious Diseases* 19:500-512 (1994).

Ochiai, Hiroshi, et al. "Infection Enhancement of Influenza A NWS Virus in Primary Murine Macrophages by Anti-Hemagglutinin Monoclonal Antibody." *Journal of Medical Virology* 36:217-221 (1992).

Olsen, Christopher W. "A review of feline infection peritonitis virus: molecular biology, immunophathogenesis, clinical aspects, and vaccination." *Veterinary Microbiology*, (1993).

Peiris, J.S.M. J.S. Porterfield "Antibody-dependent Enhancement of Plaque Formation on Cell Lines of Macrophage Origin-A Sensitive Assay for Antiviral Antibody." *Journal of General Virology* 57:119-125 (1981).

Peiris, J.S.M. et al. "Monoclonal anti-FC receptor IgG blocks antibody enhancement of viral replication in macrophages." *Nature* 289(Jan. 15):189-191 (1981).

Porterfield, "Antibody-dependent Enhancement of Viral Infectivity," *Advances in Virus Research* 31: 335-354 (1986).

Nadler et al., "Monoclonal antibody identifies a new Ia-like (p. 29, 34) polymorphic system linked to the HLA-D/DR region," *Nature* 290: 591 (1981).

Pushko et al., "Replicon-Helper Systems from Attenuated Venezuelan equine Encephalitis Virus: Expression of Heterologous Genes in Vitro and Immunization against Heterologous Pathogens in Vivo," *Virology* 239: 389-401 (1997).

Raabe et al., "In Vitro Antibody-Dependent Enhancement Assays are Insensitive Indicators of in Vivo Vaccine Enhancement of Equine Infectious Anemia Virus," *Virology* 259: 416-427 (1999).

Schlesinger, Jacob J. Michael W. Brandriss "17D Yellow Fever Virus Infection of P388D, Cells Mediated by Monoclonal Antibodies: Properties of the Macrophage Fc Receptor." *Journal of General Virology* 64: 1255-1262 (1983).

Steinman, "The Dendritic Cell System and its Role in Immunogenicity." *Annual Review of Immunology*. 9: 271-296 (1991).

Vennema et al., "Early Death after Feline Infectious Peritonitis Virus Challenge due to Recombinant Vaccinia Virus Immunization," *Journal of Virology* 64(3): 1407-1409 (1990).

Yao et al., "Antibody-dependent enhancement of hantavirus infection in macrophage cell lines," *Archives of Virology* 122: 107-118 (1992).

* cited by examiner

FIG. 2A.

ANTIBODY DEPENDENT ENHANCEMENT OF VENEZUELAN EQUINE ENCEPHALITIS VECTOR INFECTION

RELATED APPLICATIONS

The present application is a National Phase application of PCT/US00/23845 filed on Aug. 30, 2000 and published in English, which claims priority from Application U.S. 60/177,435 filed on Jan. 21, 2000 and Application U.S. 60/151,718 filed on Aug. 31, 1999, the disclosures of which are incorporated by reference herein in their entireties.

STATEMENT OF FEDERAL SUPPORT

The present invention was made with government support under grant number DAMD17-94-J-4430 from the United States Army Research and Development Command, and grant number F32-AI09778 from the National Institute of Health. The United States government has certain rights to this invention.

FIELD OF THE INVENTION

The present invention relates to methods and compositions for delivery of nucleic acids, more particularly, alphavirus vectors and methods of administering the same.

BACKGROUND OF THE INVENTION

The Alphavirus genus includes a variety of viruses, all of which are members of the Togaviridae family. The alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1-nsP4) and the second encodes the viral structural proteins (Strauss and Strauss, (1994) *Microbiological Rev.* 58:491-562, 494). Structural subunits consisting of a single viral protein, C, associate with themselves and with the RNA genome in an icosahedral nucleocapsid. In the virion, the capsid is surrounded by a lipid envelope covered with a regular array of transmembranal protein spikes, each of which consists trimers of E1 and E2 heterodimers (see Paredes et al., *Proc. Natl. Acad. Sci. USA* (1993) 90:9095-99; Paredes et al., (1974) *Virology* 187:324-32; Pedersen et al., (1974) *J. Virol.* 14:40).

It is well known that live, attenuated viral vaccines are among the most successful means of controlling viral disease. However, for some virus pathogens, immunization with a live virus strain may be either impractical or unsafe. Attenuated, live virus vaccines are recognized as one of the most potent approaches to stimulating a protective immune response to pathogens and have been employed with success in the prevention of infectious diseases. Live virus vaccine vectors utilize the same advantages, stimulating both cytolytic T lymphocyte (CTL) activity and antibody production, without the danger of revertent virulent virus. Venezuelan equine encephalitis virus (VEE) derived vaccine vectors expressing heterologous genes have been developed with success in murine and primate models to protect against challenge with influenza virus (N. L. Davis et al., (1996) *J. Virol.* 70:3781-7), simian immunodeficiency virus (SIV; N. L. Davis et al., (2000) *J. Virology* 74:371) and Marburg virus (M. Hevey et al., (1998) *Virology* 251:2837).

In addition, live virus, non-propagating VEE replicon particles (VRP), expressing heterologous antigens, successfully protect against a lethal challenge of influenza in mice (P. Pushko et al., (1997) *Virology* 239:389-401) and SIV in primates (N. L. Davis et al., (2000) *J. Virology* 74:371).

Antibody-dependent enhancement (ADE) is a phenomenon wherein antibodies enhance, rather than inhibit, virus infectivity and pathogenesis. According to the classical theory of ADE, subneutralizing titers of neutralizing antiviral antibodies form complexes with the virus, which then associate with Fc immunoglobulin and/or complement receptors on macrophages and monocytes. This interaction is believed to result in increased viral infection of these cells (see, e.g., Hawkes et al., (1967) *Virology* 33:250). In some instances, there is a correlation between ADE and disease, most notably the "dengue shock syndrome" that is associated with infection by dengue viruses (Morens, (1994) *Clin. Infectious Diseases* 19:500). More recently, it has been proposed that ADE is involved in the pathogenesis of human immunodeficiency virus (HIV) and feline infectious peritonitis virus (FIPV) (see, e.g., Füst, (1997) *Parasitology* 15 (Suppl): S127; Olsen, (1993) *Veterinary Microbiology* 36:1).

ADE has been reported in cultured cells in connection with a wide variety of viruses, including flaviviruses, such as Dengue virus, West Nile virus, Murray Valley encephalitis virus, and Yellow fever virus; alphaviruses, such as tick-borne encephalitis virus, Semliki Forest virus, Western equine encephalitis virus, and Sindbis virus; lactate dehydrogenase virus; human respiratory syncytial virus; influenza A virus; rabies virus; feline infectious peritonitis virus (FIPV), human- and feline-immunodeficiency virus (HIV, FIV), and murine cytomegalovirus. (Olsen, (1993) *Veterinary Microbiology* 36:1; Peiris et al., (1981) *J. Gen. Virol.* 57:119).

Dendritic cells (DC) are postulated to play important roles in antigen presentation and initiation of several T cell dependent immune responses. DC have been demonstrated to be more potent antigen-presenting cells (APC) than are macrophages or monocytes. Moreover, it has been reported that DC stimulate T cell proliferation up to ten-fold more efficiently than do monocytes (Guyre et al., (1997) *Cancer Immunol Immunother.* 45:146, 147 col. 2). Accordingly, it would be desirable to target antigens or other therapeutic molecules to DC to produce an enhanced immune response, in particular, to improve the efficacy of vaccines and immunotherapeutic regimes.

SUMMARY OF THE INVENTION

The present invention is based, in part, on the discovery that the efficacy of alphavirus vectors (e.g., VEE vectors) may be enhanced (e.g., improved, increased, and the like) in the presence of antibodies directed against the alphavirus. In particular, the infectivity of particular cells by alphavirus vectors may be enhanced in the presence of antibodies against the alphavirus. Moreover, the interaction of the antibody with the alphavirus vector may target the alphavirus to antigen-presenting cells (APC), preferably dendritic cells (DC). Accordingly, the present invention provides improved formulations and methods for producing an immune response in a subject (e.g., against a pathogen or against a cancer or tumor antigen) and for delivering nucleic acids to APC (e.g., nucleic acids encoding immunogenic or therapeutic proteins or peptides).

These and other aspects of the invention are set forth in more detail in the description of the invention below.

BRIEF DESCRIPTION OF THE DRAWINGS

FIG. 2A-B presents photomicrographs and FACS analysis demonstrating that VEE-specific antibodies enhance infection of VEE in bone marrow-derived cells. A. Micrograph of BM-NS cells infected with GFP-VRP-3000 alone or VRP-3000 pre-incubated in either control normal rabbit serum (NRbS) or rabbit anti-VEE serum (Rb anti-VEE). B. Percent of GFP-positive BM-NS cells as determined by FACS analysis 18 hr following either mock infection, infection with GFP-VRP-3000, or GFP-VRP-3000 at an MOI of 1.0 pre-incubated in negative control serum or rabbit anti-VEE serum (1/800).

DETAILED DESCRIPTION OF THE INVENTION

Figure 1:
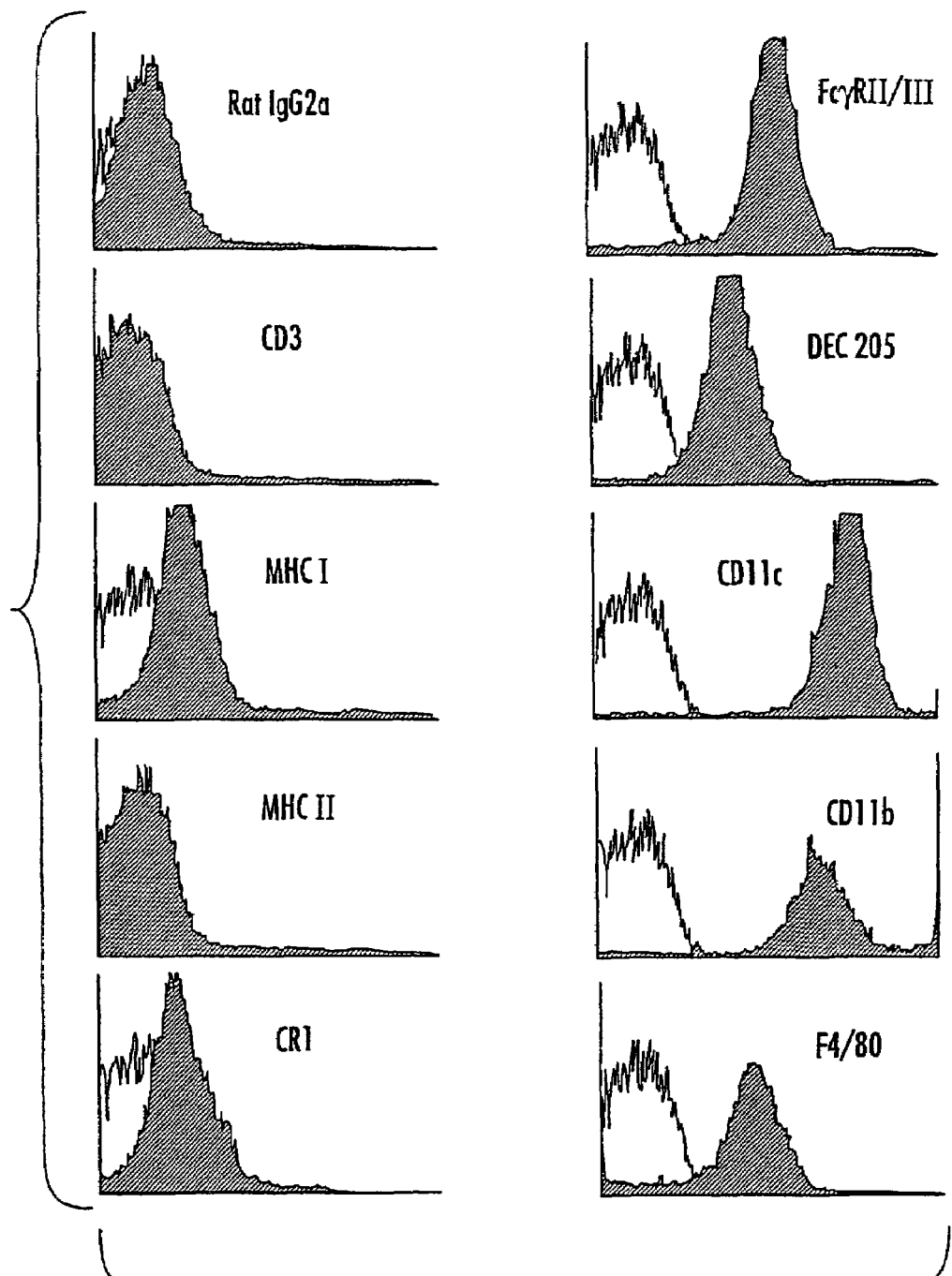
FIG. 1 shows a FACS analysis demonstrating that BM derived cells share monocyte and dendritic cell markers.

The present invention is based, in part, on the discovery that the efficacy of alphavirus vectors (e.g., VEE vectors) may be enhanced (e.g., improved, increased, augmented, and the like) in the presence of antibodies directed against the alphavirus as compared with the efficacy in the absence of the enhancing antibody. For example, an enhanced immune response may be elicited against an immunogen encoded by a heterologous nucleotide sequence carried by the alphavirus vector as compared with the efficacy in the absence of the enhancing antibody. In addition, the infectivity of a particular cell(s) by the alphavirus vector may be enhanced in the presence of an antibody against the alphavirus as compared with the efficacy in the absence of the enhancing antibody. Moreover, the interaction of the antibody with the alphavirus vector may target the alphavirus to a particular cell type(s), e.g., antigen-presenting cells (APC), such as dendritic cells (DC), as compared with the efficacy in the absence of the enhancing antibody. Accordingly, the present invention provides improved formulations and methods for producing an immune response in a subject (e.g., against a pathogen or against a cancer or tumor antigen) and for delivering nucleic acids to cells (e.g., nucleic acids encoding immunogenic or therapeutic proteins or peptides).

As used herein, the terms "enhanced" or "enhancing" indicate an increase, augmentation and/or improvement as compared with the response observed in the absence of the enhancing antibodies of the invention.

Antibody-dependent enhancement (ADE) of certain viruses is a known phenomenon typically characterized by subneutralizing titers of antibody or non-neutralizing antibodies resulting in an enhancement, rather than neutralization, of virus infectivity of macrophages and monocytes. ADE is postulated to be associated with several pathological states (e.g., Dengue shock syndrome or Dengue hemorrhagic fever and feline infectious peritonitis virus) that are marked by rapid elevation of viral titers and accelerated pathogenesis (Morens et al., (1994) *Clin. Infectious Diseases* 19:500; Olsen, (1993) *Veterinary Microbiology* 36:1). It is hypothesized that low concentrations of neutralizing antibodies complex with the virus, and the complex interacts with Fc receptors and/or complement receptors on the macrophage/monocytes. Binding of the alphavirus-antibody complex to cellular Fc receptors increases the concentration of virus on the cell surface, which results in enhanced infection of the cells.

Flynn et al., (1988) *Virology* 166:82, and Linn et al., (1996) *J. Gen. Virology* 77:407, have observed ADE of Sindbis and Ross River Virus infectivity, respectively, in cultured monocytes. However, these studies did not describe increased infectivity of dendritic cells (DC) in the presence of antibody. Moreover, these investigators did not report improved immunogenicity of alphavirus vaccines in vivo in the presence of antibody directed against the alphavirus.

Chanas et al., (1982) *J. Gen. Virol.* 58:37, reported enhanced infectivity by Sindbis virus of macrophage-like cells by two neutralizing monoclonal antibodies at sub-neutralizing titers. When virus was administered intracerebrally to newborn mice in conjunction with various dilutions of antibody, neutralization (rather than enhancement) of viral-induced mortality was observed.

In contrast, the present investigations have found antibody-dependent enhancement of infectivity of APC (in particular, dendritc cells) by alphavirus vectors both in vitro and in vivo. It appears that alphavirus vectors may be advantageously targeted or directed toward APC in the presence of anti-alphavirus antibodies. Moreover, there may be an enhanced immune response elicited toward heterologous antigens encoded by the alphavirus vector in the presence of the enhancing antibody. ADE of alphavirus infectivity does not appear to be associated with any significant pathology, i.e., does not have substantial adverse effects (e.g., disease, morbidity or mortality in a subject administered the alphavirus vector in the presence of the enhancing antibody). Alternatively stated, the benefits conferred by administration of the enhancing antibody outweigh the detrimental effects thereof.

Alphavirus vectors, and in particular VEE vectors, produce a stronger and more comprehensive immune response than do conventional vaccination methods. Accordingly, alphavirus vectors may successfully vaccinate against weak antigens where other vaccination methods have failed. By a comprehensive immune response, it is meant that vaccination with alphavirus vectors, in particular VEE vectors, induces an advantageous balance of both cellular and humoral immune responses. Thus, for example, alphavirus vectors can be used to induce an immune response against a cancer or tumor antigen which fails to induce an effective immune response, although already present in the cancer cells. Likewise, the present invention is particularly useful to immunize against chronic or latent infectious disease agents, as defined below.

Except as otherwise indicated, standard methods known to those skilled in the art may be used for the construction of alphavirus vectors, viral infection of cells, production of attenuated viruses, and production of antibodies. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al CURRENT PROTOCOLS IN MOLECULAR BIOLOGY (Green Publishing Associates, Inc. and John Wiley & Sons, Inc., New York).

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

I. Antibody-Dependent Enhancement of Alphavirus Infectivity.

In one particular embodiment, the present invention provides a method of introducing and expressing a nucleotide sequence in a cell, comprising contacting the cell with an alphavirus vector carrying a heterologous nucleotide sequence in the presence of an antibody that enhances the infectivity of the vector. Preferably, the cell is contacted with an alphavirus vector comprising a heterologous nucleotide sequence and an antibody that specifically binds to the alphavirus vector, so that the heterologous nucleotide sequence is introduced into and, preferably, expressed in the cell.

By "contacting" a cell with an alphavirus vector and an antibody that specifically binds to the alphavirus vector, as used herein, it is intended that the cell is contacted with both the alphavirus vector and the antibody. Typically, both the alphavirus vector and the antibody vector are bound to the cell as a result of contacting the cell. While not wishing to be held to any particular theory of the invention, it is thought that both the alphavirus vector and the antibody will, at least transiently, be bound to the cell at the same time, although not necessarily to each other. Alternatively, the antibody may bind to the cell first and induce a change in the cell that enhances the efficacy of the alphavirus vector. The alphavirus vector may bind to the cell first, and the antibody may bind to the cell subsequently, or vice versa. Alternatively, the alphavirus vector and antibody may bind to the cell essentially simultaneously. In particular embodiments, the alphavirus vector and antibody forms a complex, and the complex contacts and binds to the cell, as described below. Alternatively, a complex may be formed between the alphavirus vector and the antibody after one or both have bound to the cell.

By "bind", "binding" and "bound", it is not necessarily intended that the alphavirus vector or the antibody directly bind to the cell. For example, the antibody may first bind to the cell (e.g., at the Fc receptor) and the alphavirus vector may bind to the antibody to form a complex, and thereby be indirectly "bound" to the cell. Likewise, the alphavirus vector may first bind to the cell, and the antibody binds to the alphavirus vector that is already bound to the cell to form a complex therewith. As a further alternative, the alphavirus vector and antibody may bind to the cell at separate sites (e.g., at their respective receptors), and may optionally bind to each other to form a complex.

In other preferred embodiments, the alphavirus vector is contacted with an antibody that specifically binds to the alphavirus to form a complex between the alphavirus vector and the antibody, and the cell is contacted with the complex. It is also preferred that the complex formed between the alphavirus vector and the antibody is present in an amount that is sufficient to infect the cell, and results in expression of the heterologous nucleotide sequence in the cell.

An "enhancing" antibody according to the present invention is an antibody that specifically binds to an alphavirus vector (i.e., the antigen binding domain of the antibody binds to the alphavirus vector) and thereby increases, augments and/or improves one or more characteristics of an alphavirus vector. The antibody preferably enhances the infectivity of the virus, preferably for APC, more preferably for DC, as compared with the level observed in the absence of the enhancing antibody. In addition, the antibody preferably targets or directs the alphavirus to particular cells, more preferably APC, still more preferably DC, as compared with the level observed in the absence of the enhancing antibody. It is further preferred that the antibody enhances or increases the immune response (more preferably, T cell mediated immune response) mounted against an antigen encoded by the alphavirus vector as compared with the level observed in the absence of the enhancing antibody.

Preferably, the antibodies of the present invention are not bispecific or "bridging" antibodies as are known in the art (see, e.g., Wickham et al., (1996) *J. Virology* 70:6831; U.S. Pat. No. 5,695,991 to Lindholm et al.; international patent publication WO 99/00511; U.S. Pat. No. 5,861,156 to George et al.; and Bartlett et al., (1999) *Nat. Biotechnol.* 17: 181). In other words, it is preferred that the antibody does not specifically bind (i.e., via the antigen binding domain) to both the alphavirus vector and a cellular epitope to effect viral entry into the cell. Likewise, it is preferred that the antibody directed against the alphavirus vector does not also specifically bind to (i.e., via the antigen binding domain), or is not otherwise conjugated to, a ligand for a cellular receptor.

The antibodies of the invention are directed against the alphavirus vector, preferably the virion of the alphavirus vector (e.g., the antibody binds to the E1 glycoprotein and/or the E2 glycoprotein). In other words, according to this embodiment, the antibody recognizes an epitope(s) on the alphavirus, more preferably an epitope(s) in the alphavirus structural proteins, most preferably, in the alphavirus E1 glycoprotein and/or the alphavirus E2 glycoprotein. It is also preferred that the antibodies are anti-VEE antibodies.

It is further preferred that the antibody binds the alphavirus with high affinity, e.g., with a dissociation constant of at least about $10^{-6}$, preferably at least about $10^{-7}$, more preferably at least about $10^{-6}$, still more preferably at least about $10^{-9}$. Alternatively stated, the antibody specifically binds to the alphavirus (as opposed to non-specific interactions). As used herein, the term "specifically binds to the alphavirus" is not intended to indicate that the antibody only binds to that particular alphavirus (e.g., does not bind to other alphaviruses), although in particular embodiments, this may be the case.

Those skilled in the art will appreciate that the antibody may be neutralizing for alphavirus infection at sufficiently high concentrations. In addition, the antibody may by neutralizing in some cell types (e.g., BHK cells) even at concentrations at which ADE is observed in other cells types (e.g., DC). This phenomenon is contrary to most observations of ADE in the art, wherein ADE is typically believed to occur at sub-neutralizing titers of a neutralizing antibody (see, e.g., Hawkes et al., (1967) *Virology* 33:250). In contrast, the present investigations have found ADE of alphavirus infectivity of cells (e.g., DC) at concentrations of alphavirus that are neutralizing in other cell types (e.g., BHK cells).

The antibody is preferably present in an "enhancing" amount that is sufficient to increase or augment infectivity of the alphavirus vector in a cell as compared with the levels observed in the absence of the enhancing antibody. It is also preferred that the antibody is present in an "enhancing" amount that increases or augments an immune response to a heterologous antigen encoded by the vector as compared with the levels observed in the absence of the enhancing antibody, but insufficient to neutralize the alphavirus vector in said cell. It is also preferred that the antibody is present in an "enhancing" amount that is sufficient to target the infectivity of the alphavirus vector, e.g., toward APC, more preferably DC, as compared with the levels observed in the absence of the enhancing antibody. Those skilled in the art will appreciate that the concentration of the enhancing antibody to be used will depend on several factors including: the nature of the antibody, the alphavirus, and the antigen, the condition of the subject, and the desired result. Enhancing concentrations of anti-alphavirus antibodies may be routinely determined using the present description as a guide.

The term "antibody" or "antibodies" as used herein refers to all types of immunoglobulins, including IgG, IgM, IgA, IgD, and IgE. Of these, IgG are particularly preferred. The antibodies may be monoclonal or polyclonal and may be of any species of origin, including (for example) mouse, rat, rabbit, horse, or human, or may be chimeric antibodies (see, e.g., M. Walker et al., (1989) *Molec. Immunol.* 26, 403-11). The antibodies may be recombinant monoclonal antibodies produced according to the methods disclosed in U.S. Pat. No. 4,474,893 to Reading et al. or U.S. Pat. No. 4,816,567 to Cabilly et al. The antibodies may also be chemically constructed by specific antibodies made according to the method disclosed in U.S. Pat. No. 4,676,980 to Segal et al.

Antibodies may be polyclonal or monoclonal, with monoclonal being preferred. It is also preferred that the antibodies are human antibodies or humanized antibodies (i.e., the regions outside of the complementarity determining region (CDR) of the antibody are of human origin). Humanization of rodent monoclonal antibodies by CDR-grafting (also called "reshaping") is now a standard procedure for reducing immunogenicity and recruiting human effector functions.

Antibodies that bind to alphavirus vectors as described herein and achieve the desired ADE can be identified in accordance with known techniques by routine methods known in the art.

The term "antibody" or "antibodies" as used herein also encompasses antibody fragments. Antibody fragments included within the scope of the present invention include, for example, Fab, F(ab')2, and Fc fragments, and the corresponding fragments obtained from antibodies other than IgG. Such fragments can be produced by known techniques.

Polyclonal antibodies used to carry out the present invention may be produced by immunizing a suitable animal (e.g., rabbit, goat, etc.) with the particular alphavirus (or alphavirus virion or glycoprotein), collecting immune serum from the animal, and separating the polyclonal antibodies from the immune serum, in accordance with known procedures.

Monoclonal antibodies used to carry out the present invention may be produced in a hybridoma cell line according to the technique of Kohler and Milstein, *Nature* 265, 495-97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity. Monoclonal Fab fragments may be produced in *Escherichia coil* by recombinant techniques known to those skilled in the art. See, e.g., W. Huse, *Science* 246, 1275-81 (1989).

Enhancing antibodies against alphaviruses may also be obtained by phage display techniques known in the art.

The antibody may be provided to the cell by any suitable method. For example, the antibody may be an exogenous antibody that is isolated or synthesized and provided to the cell. In particular preferred embodiments, the alphavirus vector and antibody may be combined into a formulation, and the cell is contacted with this formulation. Alternatively, the alphavirus vector is contacted with the cell prior to the antibody, or vice versa. As a further alternative, the cell may be concurrently contacted with the alphavirus vector and the antibody as separate formulations.

For in vivo applications, the alphavirus vector may be administered with an exogenous antibody of the invention. The antibody may be administered to the subject prior to, subsequent to, or concurrently with the alphavirus vector. "Concurrent administration" is used herein to mean administration within hours, preferably minutes, of the same time, not necessarily at the same precise moment. Concurrent administration may be carried out by combining the alphavirus vector and antibody prior to administration, preferably in a pharmaceutically acceptable carrier, or by substantially simultaneous co-administration of the alphavirus and antibody, at the same or at different sites. Alternatively, the antibody may be administered prior to administration of the alphavirus, provided that the antibody is still present at sufficient concentrations at the time of alphavirus administration. Likewise, the alphavirus vector may be administered first, provided that it is still present at sufficient concentrations at the time of antibody administration.

Alternatively, the antibody may be provided by priming the subject with a first administration of an alphavirus vector (i.e., the subject has previously been exposed to an alphavirus vector, although the first alphavirus vector may comprise a different or no heterologous nucleotide sequence) so that the subject has antibodies that specifically bind to the alphavirus vector. An immune-competent subject will mount an immune response against the alphavirus and produce antibodies directed thereto. The antibody will thereby be present when a subsequent alphavirus vector encoding a heterologous nucleotide sequence of interest is administered. The alphavirus vector used to prime the subject need not be identical to the second alphavirus vector used to deliver the heterologous nucleotide sequence of interest, as long as the priming alphavirus vector is sufficient to evoke the production of antibodies that specifically bind to the second alphavirus vector. Preferably the first alphavirus vector and the subsequent alphavirus vector are heterologous vectors, i.e., the first alphavirus vector comprises a different heterologous nucleotide sequence from the second alphavirus vector or the first vector does not comprise a heterologous nucleotide sequence at all.

In the case of immunocompromised subjects, it is preferable to provide an antibody from exogenous sources (as described hereinabove), rather than relying on the subject's immune system to produce enhancing antibodies.

In addition, exogenous antibody may advantageously be provided in those situations in which a more rapid and aggressive treatment is desired, i.e., when it would be undesirable to wait for the subject to mount an immune response and produce anti-alphavirus antibodies.

The present invention may be practiced with any cell known in the art in which antibody-enhanced infectivity of the alphavirus is observed. Additionally, the present invention may be practiced with any cell in which antibody-mediated targeting of alphavirus vectors is observed. The present invention may further be practiced in any suitable cell in which an enhanced immune response is observed against an immunogen encoded by the alphavirus vector in the presence of the enhancing antibody.

Typically, the cell will be one that is permissive for alphavirus infection, although cells that are only permissive in the presence of enhancing antibody are also suitable. In preferred embodiments, the cell is an antigen-presenting cell (APC). As used herein, the term "APC" refers to cells that present antigens to T cells, including but not limited to macrophages, monocytes, dendritic cells, phagoctyic leukocytes, B lymphoctyes, and endothelial cells. Typically, APC express MHC class II antigens on the cell surface. More preferably, the cell is a dendritic cell (DC), including DC precursors such as Langerhans cells.

DC are a system of antigen-presenting cells that function to initiate several immune responses such as the sensitization of MHC-restricted T cells, the rejection of organ transplants, and the formation of T cell-dependent antibodies. DC are found in many non-lymphoid tissues but can migrate via the afferent lymph or the blood stream to the T cell-dependent areas of lymphoid organs. They are found in the skin, where they are called Langerhans cells, and are also present in the mucosa. DC are believed to function within the peripheral tissues where they acquire antigens for presentation to the immune system.

DC appear to play a crucial role in the initiation of T-cell dependent responses. These cells bind and modify antigens in a manner such that the modified antigen, when presented on the surface of the DC, can activate T-cells to participate in the production of antibodies. The modification of antigens by DC may, for example, include fragmenting the protein to produce peptides that have regions that are highly activating for T-cells.

DC are distributed widely throughout the body, as reviewed by Steinman, (1991)*Ann. Rev. Immunol.* 9:271. These cells have been identified in non-lymphoid organs either close to body surfaces, as in the skin and airways, or in interstitial regions of organs such as heart and liver. DC can migrate via the blood and lymph to lymphoid organs where antigens can be presented to T cells in the recirculating pool. DC, or their precursors, are found in lymphoid organs (e.g., tonsils, thymus, spleen), the circulation (e.g., afferent lymph veiled cells, blood DC), and nonlymphoid organs (epidermis, heart, liver, lung, gut). DC are also found in bone marrow and epidermis (where precursors are called "Langerhans cells"). Cells known in the art as "interdigitating cells", "veiled cells", and "interstitial DC" are also encompassed by the term "DC" as used herein. The present invention is preferably carried out with DC of the bone marrow and/or epidermis (e.g., Langerhans cells).

DC may be cultured in vitro (including for ex vivo applications) as described in detail herein. Alternatively, any other suitable method known in the art may be employed, including the techniques described in U.S. Pat. No. 6,004,807 to Banchereau et al. and U.S. Pat. No. 5,994,126 to Steinman et al., which are incorporated by reference herein in their entirety.

In particular preferred embodiments, the cell expresses Fc immunoglobulin receptors (FcR), which bind to the Fc region of immunoglobulins. FcR are membrane-associated glycoproteins and are members of the immunoglobulin superfamily. Distinct receptors are expressed for each isotype of antibody (e.g., Fcγ, Fcε, Fcα, Fcμ, Fcδ and the like). It is now established that the diversity of cellular responses triggered by antibodies and immune complexes results from the structural heterogeneity of Fc receptors.

It is preferred that the cell is one that expresses Fcγ receptors (IgG Fc receptors), still more preferably FcγII/III receptors. Among the FcγR, three classes of molecules have been defined, varying in structure and affinity for IgG. Exemplary FcγR include FcγRI (e.g., FcγRA, FcγRB and FcγRIC), FcγRII (e.g., FcγRIIA, FcγRIIB and FcγRIIC), and FcγRIII (e.g., FcγRIIIA or FcγRIIIB). FcγRI, present on monocytes and macrophages, is a high affinity IgG receptor. FcγRII and FcγRIII are relatively low affinity receptors and appear to only bind antibody in the form of immune complexes. FcγRII are more widely expressed by hematopoietic cells than are FcγRIII.

FcγR and FcεR couple humoral and cellular immunity by directing the interaction of antibodies with effector cells. These receptors are present on most effector cells of the immune system and mediate phagocytosis, antibody-dependent cell-mediated cytotoxicity, activation of inflammatory cells, and many of the biological sequelae associated with antibody-dependent immunity.

Cells that express FcγR include, but are not limited to, cells of hematopoietic lineage, including but not limited to, macrophages, monocytes, platelets, neutrophils, eosinophils, mast cells, natural killer cells, basophils, B cells, and DC cells. Macrophages, monocytes and DC are preferred, with DC (including Langerhans cells and other DC precursors) being more preferred. Cells expressing FcγR also include immature thymocytes and certain tumor cell lines.

In other particular embodiments, the alphavirus vector is contacted with a cell that expresses a complement receptor (e.g., complement receptor 1 (CR1), CR2, CR3, and the like). The complement system includes a group of proteins in blood plasma that play an integral role in immune and allergic reactions. Activation of complement can occur via at least two pathways. The classical pathway of complement activation involves antigen-antibody complexes. Regardless of which initiation pathway is used, the end result is the formation of activated fragments of complement proteins (e.g., C3a, C4a, C5a and C5b-9), which mediate several functions including leukoctye chemotaxis, activation of macrophages, vascular permeability, and cellular lysis. Exemplary cells that express complement receptors include, but are not limited to, dendritic cells, monocytes, macrophages, neutrophils, eosinophils, erythroctyes, B cells, T cells, epithelial cells, natural killer cells, mast cells, basophils, smooth muscle cells, lymphocytes, endothelial cells, fibroblasts, granulocytes, and microglial cells.

In particular preferred embodiments, the cell expresses both Fc and complement receptors.

In other preferred embodiments, the cell may be any stem cell or progenitor cell. Stem cells may be isolated from any organ, including but not limited to liver, muscle, bone marrow, spleen, vascular tissue, brain (and other nervous tissue), kidney, gastrointestinal tract, skin (e.g., foreskin), heart, lung and the like. Stem cells may also be isolated by any method known in the art, e.g., as described by E. Gussoni et al., (1999) *Nature* 401:390.

In still other embodiments, the cell is a cancer or tumor cell that has been removed from the subject. According to this embodiment, the cell is typically irradiated to prevent cell replication prior to administering the cell back into a subject.

The cell may be a cell in vitro, in vivo, or ex vivo (e.g., removed from a subject for manipulation and then, typically, re-introduced into the same subject). For ex vivo approaches, it is preferred that the subject's own cells are used. For example, as described hereinbelow, DC cells from a subject with cancer or a tumor may be removed, an alphavirus vector expressing a suitable cancer or tumor cell antigen introduced therein in the presence of enhancing anti-alphavirus antibodies, and the genetically manipulated DC administered to the subject. Alternatively, the cells are HLA compatible with the subject's HLA type. For example, cultured cells or cells from another subject that are HLA compatible with the recipient may be used.

The alphavirus vector carrying the heterologous nucleotide sequence is contacted with and introduced into the cell where, preferably, the nucleotide sequence is expressed. Nucleic acids of interest include nucleic acids encoding peptides and proteins, preferably immunogenic (e.g., for an immunogenic composition or a vaccine) or therapeutic (e.g., for medical or veterinary uses) peptides or proteins.

An "immunogenic" peptide or protein, or "immunogen" as used herein is any peptide or protein that elicits an immune response in a subject, more preferably, the immunogenic peptide or protein is suitable for providing some degree of protection to a subject against a disease. The present invention may be employed to express an immunogenic peptide or protein in a subject (e.g., for vaccination) or for immunotherapy (e.g., to treat a subject with cancer or tumors).

An immunogenic protein or peptide, or immunogen, may be any protein or peptide suitable for protecting the subject against a disease, including but not limited to microbial, bacterial, protozoal, parasitic, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio antigen, herpes antigen (e.g., CMV, EBV, HSV antigens) mumps antigen, measles antigen, rubella antigen, diptheria toxin or other diptheria antigen, pertussis antigen, hepatitis (e.g., hepatitis A or hepatitis B) antigen, or any other vaccine antigen known in the art.

The present invention may also be advantageously employed to produce an immune response against chronic or latent infective agents, which typically persist because they fail to elicit a strong immune response in the subject. Illustrative latent or chronic infective agents include, but are not limited to, hepatitis B, hepatitis C, Epstein-Barr Virus, herpes viruses, human immunodeficiency virus, and human papilloma viruses. Alphavirus vectors encoding antigens from these infectious agents may be administered to a cell or a subject according to the methods described herein.

Alternatively, the immunogen may be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281) and include, but are not limited to: MART-1/MelanA, gp100, tyrosinase, TRP-1, TRP-2, MAGE-1, MAGE-3, GAGE-1/2, BAGE, RAGE, NY-ESO-1, CDK4, β-catenin, MUM-1, Caspase-8, KIAA0205, HPVE&, SART-1, PRAME, p15, and p53 antigens.

The immunogen may also be a "universal" or "artificial" cancer or tumor cell antigen as described in international patent publication WO 99/51263, which is hereby incorporated by reference in its entirety.

The present invention further finds use in methods of producing antibodies in vivo for passive immunization techniques. According to this embodiment an alphavirus vector expressing an immunogen of interest is administered to a subject in the presence of an enhancing antibody, as described herein by direct administration or ex vivo cell manipulation techniques. The antibody may then be collected from the subject using routine methods known in the art. The invention further finds use in methods of producing antibodies against an immunogen expressed from an alphavirus vector for any other purpose, e.g., for diagnostic purpose or for use in histological techniques.

Alternatively, the present invention may be practiced to express a therapeutic peptide or protein in the cell, in vitro or in vivo. A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-cancer effects. Therapeutic peptides and proteins include, but are not limited to, CFTR (cystic fibrosis transmembrane regulator protein), dystrophin (including the protein product of dystrophin mini-genes, see, e.g., Vincent et al. (1993) *Nature Genetics* 5:130), utrophin (Tinsley et al. (1996) *Nature* 384:349), clotting factors (Factor XIII, Factor IX, Factor X, etc.), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, hormones, growth factors (e.g., insulin-like growth factors 1 and 2, platelet derived growth factor, epidermal growth factor, nerve growth factor, neurotrophic factor-3 and 4, brain-derived neurotrophic factor, glial derived growth factor, transforming growth factor-α and -β, and the like), cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other peptide or protein that has a therapeutic effect in a subject in need thereof.

Further exemplary therapeutic peptides or proteins include those that may used in the treatment of a disease condition including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amylotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

The present invention may be preferably, and advantageously, employed for relatively short-term therapeutic regimes. For example, immunomodulators (e.g., cytokines, as defined above) may be delivered using an alphavirus vector as described herein. Likewise, supportive therapeutic agents (e.g., immunomodulators, erythropoietin) may be provided in conjunction with chemotherapy.

As a further alternative, the alphavirus vector may be used to express an antibody against a defective or over-expressed protein. Subjects expressing the defective protein or over-expressed protein may be administered an alphavirus vector according to the invention expressing an antibody that modulates the activity of the protein.

As a further alternative, the heterologous nucleic acid sequence may encode a reporter peptide or protein (e.g., an enzyme). Reporter proteins are known in the art and include, but are not limited to, Green Fluorescent Protein, β-galactosidase, alkaline phosphatase, chloramphenicol acetyltransferase, and the like.

Alternatively, in particular embodiments of the invention, the nucleic acid of interest may encode an antisense nucleic acid, a ribozyme (e.g., as described in U.S. Pat. No. 5,877,022), RNAs that effect spliceosome-mediated trans-splicing (Puttaraju et al. (1999) Nature Biotech. 17:246), or other non-translated RNAs, such as "guide" RNAs (Gorman et al., (1998) Proc. Nat. Acad. Sci. USA 95:4929; U.S. Pat. No. 5,869,248 to Yuan et al.), and the like.

The heterologous nucleic acid may be operably associated with expression control elements, such as transcription/translation control signals, origins of replication, polyadenylation signals, and internal ribosome entry sites (IRES), promoters, enhancers, and the like. Those skilled in the art will appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence.

Promoters/enhancers that are native to the subject to be treated are most preferred. Also preferred are promoters/enhancers that are native to the heterologous nucleic acid sequence. The promoter/enhancer is chosen so that it will function in the target cell(s) of interest. Mammalian promoters/enhancers are also preferred.

Preferably, the heterologous nucleotide sequence is operably associated with a promoter that provides high level expression of the heterologous nucleotide sequence, e.g., an alphavirus subgenomic 26S promoter (preferably, a VEE 26S promoter).

In embodiments of the invention in which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

As a further aspect, the present invention provides a method of targeting an alphavirus vector of the invention to a particular cell type(s) (i.e., directing the alphavirus vector to a particular cell or cell types) comprising contacting the cell with an alphavirus vector carrying a heterologous nucleotide sequence in the presence of an enhancing antibody directed against the alphavirus. In other words, the alphavirus vector infects the cell at a higher rate than it would in the absence of the antibody. Preferably, the cell is contacted (as this term is described hereinabove) with an alphavirus vector comprising a heterologous nucleotide sequence and an antibody that specifically binds to the alphavirus vector, whereby the heterologous nucleotide sequence is introduced into and expressed in the cell.

In particular preferred embodiments, the alphavirus vector is contacted with an enhancing antibody that specifically binds to the alphavirus vector, as described above, to form a complex. According to this embodiment, the complex between the alphavirus and the enhancing antibody targets or directs the alphavirus vector to a particular cell or cell type at a higher frequency than in the absence of the enhancing antibody.

It is also preferred that the alphavirus vector is a VEE vector and the antibody is an enhancing anti-VEE antibody, as described herein.

Alphaviruses, heterologous nucleotide sequences, and antibodies are as described hereinabove. As described herein, this method may be carried out with cells in vitro, in vivo (i.e., by administration to a subject), or ex vivo. It is further preferred that the alphavirus vector is targeted to APC, more preferably DC, or to cells expressing Fc and/or complement receptors, all as described herein.

As a further aspect, the present invention provides a method of producing an immune response in a subject, comprising administering an alphavirus vector carrying a nucleotide sequence encoding an immunogen to a subject, wherein the alphavirus vector is administered in the presence of enhancing antibodies against the alphavirus, and an active immune response is mounted by the subject against the immunogen. Immunogens are as described hereinabove. The antibody may be provided by administering exogenous antibody, as described above. Alternatively, the subject may be primed to produce anti-alphavirus antibodies by previous exposure to an alphavirus vector (preferably, a heterologous alphavirus vector, i.e., a vector comprising a different heterologous nucleotide sequence or a vector that does not comprise a heterologous nucleotide sequence at all), as described hereinabove. Preferably, a protective immune response is elicited.

An "active immune response" or "active immunity" is characterized by "participabon of host tissues and cells after an encounter with the immunogen. It involves differentiation and proliferation of immunocompetent cells in lymphoreticular issues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, an alphavirus vector comprising a heterologous nucleotide sequence encoding an immunogen and an antibody that specifically binds to the alphavirus vector are administered to a subject.

In other particular preferred embodiments, the alphavirus vector is contacted with the enhancing antibody that specifically binds to the alphavirus vector to form a complex. As described hereinabove, the complex may then administered to the subject. Alternatively, the antibody may be administered prior to, or subsequent to, the administration of the alphavirus vector.

As an alternative embodiment, the antibody may be provided by the subject (e.g., by a prior immunization with an alphavirus vector to produce an immune response thereto), as described herein.

As a further alternative, the alphavirus vector may be administered to a cell ex vivo and the altered cell is administered to the subject. According to this embodiment, an alphavirus vector comprising a heterologous nucleotide sequence encoding an immunogen is contacted with a cell in the presence of an enhancing antibody that specifically binds to the alphavirus vector, as described herein. In a preferred embodiment, the cell is contacted with an alphavirus vector comprising a heterologous nucleotide sequence encoding an immunogen and an antibody that specifically binds to the alphavirus vector. The heterologous nucleotide sequence is permitted to be introduced into the cell, and the cell is administered to the subject, where the heterologous nucleotide sequence encoding the immunogen is preferably expressed and induces an immune response in the subject against the immunogen.

In another illustrative embodiment, an alphavirus vector comprising a heterologous nucleotide sequence encoding an immunogen is contacted with an antibody that specifically binds to the alphavirus vector to form a complex between the alphavirus vector and the antibody. A cell is contacted with the complex ex vivo, and the heterologous nucleotide sequence is permitted to be taken up, and preferably expressed, by the cell. The altered cell is then administered to the subject, and an active immune response is elicited in the subject against the immunogen.

According to the foregoing methods of inducing an immune response in a subject, it is preferred that the alphavirus vector carrying the heterologous nucleotide sequence is administered in an immunogenic amount, as described below.

The present invention also encompasses methods of treating cancer or tumors using immunotherapy by administration of alphavirus vectors expressing cancer or tumor cell antigens in the presence of enhancing antibodies. In one particular embodiment, an immune response may be produced against a cancer or tumor antigen in a subject by administering an alphavirus vector carrying a heterologous nucleotide sequence encoding the cancer or tumor antigen, wherein the alphavirus vector is administered in the presence of antibodies against the alphavirus, for example to treat a patient with cancer or a tumor. The alphavirus vector may be administered to a cell in vitro or to a subject in vivo or by using ex vivo methods, as described herein.

The approach disclosed herein provides a generalized strategy for treating and preventing cancers of any origin, either tumor forming or non-tumor forming cancers. The inventive methods can be used to treat both the primary cancer or tumor and to prevent metastasis. Alternatively, the inventive methods can be advantageously employed to reduce or prevent growth of metastatic nodules (e.g., following surgical removal of a primary tumor). The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers. The term "tumor" is also understood in the art, for example, as an abnormal mass of undifferentiated cells within a multicellular organism. Tumors can be malignant or benign. Preferably, the inventive methods disclosed herein are used to prevent and treat malignant tumors.

Cancer and tumor antigens according to the present invention have been described hereinabove. By the terms "treating cancer" or "treatment of cancer", it is intended that the severity of the cancer is reduced or the cancer is at least partially eliminated. Preferably, these terms indicate that metastasis of the cancer is reduced or at least partially eliminated. It is further preferred that these terms indicate that growth of metastatic nodules (e.g., after surgical removal of a primary tumor) is reduced or at least partially eliminated. By the terms "prevention of cancer" or "preventing cancer" it is intended that the inventive methods at least partially eliminate or reduce the incidence or onset of cancer. Alternatively stated, the present methods slow, control, decrease the likelihood or probability, or delay the onset of cancer in the subject.

Likewise, by the terms "treating tumors" or "treatment of tumors", it is intended that the severity of the tumor is reduced or the tumor is at least partially eliminated. Preferably, these terms are intended to mean that metastasis of the tumor is reduced or at least partially eliminated. It is also preferred that these terms indicate that growth of metastatic nodules (e.g., after surgical removal of a primary tumor) is reduced or at least partially eliminated. By the terms "prevention of tumors" or "preventing tumors" it is intended that the inventive methods at least partially eliminate or reduce the incidence or onset of tumors. Alternatively stated, the present methods slow, control, decrease the likelihood or probability, or delay the onset of tumors in the subject.

In other embodiments, cells may be removed from a subject with cancer or a tumor and contacted with an alphavirus vector (preferably, VEE vector) and an enhancing antibody directed against the alphavirus vector. Preferably, the cell is an APC, more preferably, a DC. In more preferred embodiments, DC cells are removed from a subject with cancer or a tumor, infected with a VEE vector carrying an appropriate cancer or tumor cell antigen in the presence of an enhancing anti-VEE antibody. The modified DC are then administered to the subject, whereby an immune response against the cancer or tumor antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, in particular embodiments of the invention, immunomodulatory cytokines (preferably, CTL inductive cytokines) are administered to a subject in conjunction with the methods described herein for producing an immune response or providing immunotherapy.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

In preferred embodiments, an alphavirus vector encoding a cytokine is used to deliver the cytokine to the subject. Accordingly, the present invention further provides a method of delivering a cytokine to a cell (preferably APC, more preferably DC, as described hereinabove) comprising contacting the cell with an alphavirus vector carrying a heterologous nucleotide sequence encoding the cytokine in the presence of an antibody against the alphavirus, whereby the nucleotide sequence encoding the cytokine is introduced into and expressed by the cell. This method may be employed to enhance an immune response to an antigen, e.g., a vaccine antigen or a cancer or tumor cell antigen.

In particular embodiments, an alphavirus vector encoding an antigen and a cytokine may be contacted with and introduced into a cell. Alternatively, the antigen may be delivered by one alphavirus vector, and the cytokine is introduced into the cell by means of a different alphavirus vector.

II. Alphavirus Vectors.

The present invention is practiced using alphavirus vectors, more preferably a propagation-incompetent alphavirus vector, still more preferably an alphavirus replicon vector. Alphavirus and replicon vectors are described in U.S. Pat. No. 5,505,947 to Johnston et al.; U.S. Pat. No. 5,792,462 to Johnston et al., U.S. Pat. No. 5,814,482 to Dubensky et al., U.S. Pat. No. 5,843,723 to Dubensky et al., U.S. Pat. No. 5,789,245 to Dubensky et al., U.S. Pat. No. 5,739,026 to Garoff et al., the disclosures of which are incorporated herein by reference in their entirety.

Alphavirus replicon vectors, and in particular VEE replicon vectors, elicit a strong host response to immunogen. While not wishing to be held to any particular theory of the invention, it appears that alphavirus replicon vectors induce a more balanced and comprehensive immune response (i.e., cellular and humoral immunity) than do conventional vaccination methods. Moreover, it appears that alphavirus vectors induce a strong immune response, in part, because they directly infect and replicate within dendritic cells. The resulting presentation of antigen to the immune system induces a strong immune response. The alphavirus 26S subgenomic promoter also appears to give high level of expression of a heterologous nucleic acid encoding antigen. VEE vectors are able to induce an immune response in recipient animals greater than that seen in animals actually infected with the corresponding infectious organism or virus.

The alphavirus vector preparation may be partially or highly purified, or may be a relatively crude cell lysate or supernate from a cell culture, as known in the art.

The term "alphavirus" has its conventional meaning in the art, and includes Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86 (S.A.AR86), Girdwood S. A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzlagach virus, Highlands J virus, Fort Morgan virus, Ndumu virus, Buggy Creek virus, and any other virus classified by the International Committee on Taxonomy of Viruses (ICTV) as an alphavirus. The preferred alphavirus for use in the present invention is VEE.

An "Old World alphavirus" is a virus that is primarily distributed throughout the Old World. Alternately stated, an Old World alphavirus is a virus that is primarily distributed throughout Africa, Asia, Australia and New Zealand, or Europe. Exemplary Old World viruses include SF group alphaviruses and SIN group alphaviruses. SF group alphaviruses include Semliki Forest virus, Middelburg virus, Chikungunya virus, O'Nyong-Nyong virus, Ross River virus, Barmah Forest virus, Getah virus, Sagiyama virus, Bebaru virus, Mayaro virus, and Una virus. SIN group alphaviruses include Sindbis virus, South African Arbovirus No. 86, Ockelbo virus, Girdwood S. A. virus, Aura virus, Whataroa virus, Babanki virus, and Kyzylagach virus.

Preferred are alphaviruses including attenuating mutations. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., a loss of virulence), in accordance with standard terminology in the art. See, e.g., B. Davis et al., MICROBIOLOGY 132 (3d ed. 1980). The phrase "attenuating mutation" excludes mutations or combinations of mutations which would be lethal to the virus.

Appropriate attenuating mutations will be dependent upon the alphavirus used. Suitable attenuating mutations within the alphavirus genome will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of which are incorporated herein in their entirety by reference.

When the alphavirus capsid is from VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine or histidine as E2 amino acid 209; codons at E1 amino acid 272 which specify an attenuating amino acid, preferably threonine or serine as E1 amino acid 272; codons at E1 amino acid 81 which specify an attenuating amino acid, preferably isoleucine or leucine as E1 amino acid 81; codons at E1 amino acid 253 which specify an attenuating amino acid, preferably serine or threonine as E1 amino acid 253; or the deletion of E3 amino acids 56-69, or a combination of the deletion of E3 amino acids 56-59 together with codons at E1 amino acid 253 which specify an attenuating mutation, as provided above.

When the alphavirus is the South African Arbovirus No. 86 (S.A.AR86), exemplary attenuating mutations in the structural and non-structural proteins include, but are not limited to, codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid 372 which specify an attenuating amino acid, preferably leucine, at E2 amino acid residue 372; codons at E2 amino acid position 376 which specify an attenuating amino acid, preferably alanine as E2 amino acid 376; in combination, codons at E2 amino acid residues 304, 314, 372 and 376 which specify attenuating amino acids, as described above; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372; in combination, codons at nsP2 amino acid residues 96 and 372 which encode attenuating amino acids at nsP2 amino acid residues 96 and 372, as described above; codons at nsP2 amino acid residue 529 which specify an attenuating amino acid, preferably leucine, at nsP2 amino acid residue 529; codons at nsP2 amino acid residue 571 which specify an attenuating amino acid, preferably asparagine, at nsP2 amino acid residue 571; codons at nsP2 amino acid residue 682 which specify an attenuating amino acid, preferably arginine, at nsP2 amino acid residue 682; codons at nsP2 amino acid residue 804 which specify an attenuating amino acid, preferably arginine, at nsP2 amino acid residue 804; codons at nsp3 amino acid residue 22 which specify an attenuating amino acid, preferably arginine, at nsP3 amino acid residue 22; and in combination, codons at nsP2 amino acid residues 529, 571, 682 and 804 and at nsP3 amino acid residue 22 which specify attenuating amino acids, as described above.

Also preferred are alphavirus vectors in which there is a mutation in the capsid protease that reduces, preferably ablates, the autoprotease activity of the capsid and results, therefore, in non-viable virus. Capsid mutations that reduce or ablate the autoprotease activity of the alphavirus capsid are known in the art, see e.g., WO 96/37616 to Johnston et al., the disclosure of which is incorporated herein in its entirety. In particular embodiments, the alphavirus vector comprises a VEE virion or VEE capsid proteins in which the capsid protease is ablated, e.g., by introducing an amino acid substitution at VEE capsid position 152, 174, or 226.

Mutations may be introduced into the alphavirus vector by any method known in the art. For example, mutations may be introduced into the alphavirus RNA by performing site-directed mutagenesis on the cDNA which encodes the RNA, in accordance with known procedures. See, Kunkel, Proc. Natl. Acad. Sci. USA 82, 488 (1985), the disclosure of which is incorporated herein by reference in its entirety. Alternatively, mutations may be introduced into the RNA by replacement of homologous restriction fragments in the cDNA which encodes for the RNA, in accordance with known procedures.

The alphavirus vector may be a chimeric alphavirus, as that term is understood in the art. For example, the alphavirus virion (i.e., the structural proteins) may be from one alphavirus (preferably, VEE) and the nucleic acid packaged within the capsid be from another alphavirus, or any other virus. Alternatively, the alphavirus virus may be assembled from structural proteins derived from more than one alphavirus.

According to particular embodiments, it is desirable to employ an alphavirus vector that encodes two or more (e.g., two, three, four, five, etc.) heterologous nucleic acid sequences, preferably each encoding an antigen according to the present invention. Each heterologous nucleic acid sequence will typically be operably associated with a promoter. Alternatively, an internal ribosome entry site (IRES) sequence(s) can be placed downstream of a promoter and upstream of the heterologous nucleic acid sequence(s). The heterologous nucleic acid sequences can be associated with a constitutive or inducible promoter. The alphavirus 26S subgenomic promoter is preferred, with the VEE 26S subgenomic promoter being most preferred.

In particular preferred embodiments, the alphavirus vector encodes one or more immunogens and one or more cytokines (both as described hereinabove).

III. Gene Transfer Technology.

The methods of the present invention provide a means for delivering heterologous nucleic acid sequences into a broad range of host cells. The vectors and other reagents, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood-disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

The instant invention may also be employed to provide an antisense nucleic acid to a cell in vitro or in vivo. Expression of the antisense nucleic acid in the target cell diminishes expression of a particular protein by the cell. Accordingly, antisense nucleic acids may be administered to decrease expression of a particular protein in a subject in need thereof. Antisense nucleic acids may also be administered to cells in vitro to regulate cell physiology, e.g., to optimize cell or tissue culture systems. The present invention is also useful to deliver other non-translated RNAs, e.g., ribozymes (e.g., as described in U.S. Pat. No. 5,877,022), RNAs that effect spliceosome-mediated trans-splicing (Puttaraju et al., (1999) *Nature Biotech.* 17:246), or "guide" RNAs (see, e.g., Gorman et al., (1998) *Proc. Nat. Acad. Sci. USA* 95:4929; U.S. Pat. No. 5,869,248 to Yuan et aL) to a target cell.

Finally, the instant invention finds further use in diagnostic and screening methods, whereby a gene of interest is transiently or stably expressed in a cell culture system, or alternatively, a transgenic animal model.

IV. Subjects, Pharmaceutical Formulations, Vaccines, and Modes of Administration.

The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, primates, bovines, ovines, caprines, porcines, equines, felines, canines, lagomorphs, rodents (e.g., rats and mice), etc. Human subjects are the most preferred. Human subjects include fetal, neonatal, infant, juvenile and adult subjects. The subject may have previous exposure to alphavirus vectors and produce antibodies thereto or may be naïve subjects, as that term is used in the art.

In particular embodiments, the present invention provides a pharmaceutical composition comprising an alphavirus vector and an enhancing anti-alphavirus antibody of the invention in a pharmaceutically-acceptable carrier or other medicinal agents, pharmaceutical agents, carriers, adjuvants, diluents, etc. In particular embodiments, the antibody may be specifically bound to the alphavirus vector to form a complex. Preferably, the antibody is present in an "enhancing" amount, as described herein. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell that has been infected and genetically modified by an alphavirus vector in the presence of an enhancing antibody in a pharmaceutically-acceptable carrier or other medicinal agents, pharmaceutical agents, carriers, adjuvants, diluents, etc.

By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering the alphavirus/antibody compositions or cells directly to a subject.

The alphavirus vectors of the invention may be administered to elicit an immunogenic response (e.g., as an immunogenic composition or as a vaccine or for immunotherapy). Typically, immunological compositions of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. Typically, an amount of about $10^3$ to about $10^{15}$ virus particles, preferably about $10^4$ to about $10^{10}$, and more preferably about $10^4$ to $10^6$ virus particles per dose is suitable, depending upon the age and species of the subject being treated, and the immunogen against which the immune response is desired. Subjects and immunogens are as described above.

Typically, the present invention permits lower dosages of the alphavirus vector and/or the expressed antigen to be administered to achieve an effective immune response.

The terms "vaccination" or 'immunization' are well-understood in the art. For example, the terms vaccination or immunization can be understood to be a process that increases an subject's immune reaction to antigen and therefore to resist or overcome infection. In the case of the present invention, vaccination or immunization may also increase the organism's immune response and resistance to invasion by cancer or tumor cells.

Any suitable vaccine and method of producing an immune response (i.e., immunization) known in the art may be employed in carrying out the present invention, as long as an active immune response (preferably, a protective immune response) against the antigen is elicited.

Vaccination can be by any means known in the art, as described below, but is preferably by parenteral routes (e.g., subcutaneous, intracerebral, intradermal, intramuscular, intravenous, intraarticular), most preferably by subcutaneous injection. The dose of virus is not critical as long as it is sufficient to induce an active immune response to the expressed antigen.

The present invention further provides a method of delivering a nucleic acid to a cell (e.g., to produce an immune response or for therapy). For in vitro methods, the virus may be administered to the cell by standard viral transduction methods, as are known in the art, in the presence of an enhancing antibody. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation.

In particular embodiments of the invention, cells are removed from a subject, the alphavirus vector is introduced therein, and the cells are then replaced back into the subject. Methods of removing cells from subject for treatment ex vivo, followed by introduction back into the subject are known in the art. Alternatively, the alphavirus vector is introduced into cells from another subject, into cultured cells, or into cells from any other suitable source, and the cells are administered to a subject in need thereof. Preferably, if the subject's own cells are not used, the cells are HLA compatible with the subject's HLA type.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "immunogenic amount" (as described hereinabove) or a "therapeutically-effective amount".

A "therapeutically-effective" amount as used herein is an amount that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of treating subjects in vivo with the inventive alphavirus particles. Administration of the alphavirus particles of the present invention to a human subject or an animal in need thereof can be by any means known in the art for administering virus vectors.

Dosages of the inventive alphavirus particles will depend upon the mode of administration, the disease or condition to be treated, the individual subject's condition, the particular virus vector, and the gene to be delivered, and can be determined in a routine manner. Exemplary doses for achieving therapeutic effects are virus titers of at least about $10^5$, $10^6$, $10^7$, $10^{18}$, $10^9$, $10^{10}$, $10^{11}$, $10^{12}$, $10^3$, $10^{14}$, $10^{15}$ transducing units or more, preferably about $10^8$-$10^{13}$ transducing units.

Dosages of the antibody directed against the alphavirus vector for in vitro, in vivo, or ex vivo applications may be routinely determined. The antibody is preferably present in an "enhancing amount" that is sufficient to enhance infectivity of the alphavirus vector, more preferably the immune response to the heterologous antigen encoded by the vector, but insufficient to neutralize the alphavirus vector. It is also preferred that the antibody is present in an "enhancing" amount that is sufficient to target or direct the alphavirus particle to a particular cell type(s). Those skilled in the art will appreciate that the concentration of the enhancing antibody to be used will depend on several factors, including: the nature of the antibody, the alphavirus, and the antigen, the condition of the subject, and the desired result.

Exemplary modes of administration for alphavirus vectors, antibodies, and cells according to the present invention include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer these reagents in a local rather than systemic manner, for example, in a depot or sustained-release formulation.

In other preferred embodiments, the alphavirus, antibodies or cells are administered intramuscularly, more preferably by intramuscular injection or by local administration (as defined above).

In other preferred embodiments, the alphavirus vectors of the present invention are administered to the lungs. The alphavirus vectors disclosed herein may be administered to the lungs of a subject by any suitable means, but are preferably administered by administering an aerosol suspension of respirable particles comprised of the inventive alphavirus vectors, which the subject inhales. The respirable particles may be liquid or solid. Aerosols of liquid particles comprising the inventive alphavirus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

The following examples are provided to illustrate the present invention, and should not be construed as limiting thereof.

EXAMPLE 1

Materials and Methods

Virus: VEE replicon particles (VRP) expressing either influenza virus hemagglutinin (HA-VRP-3000 and HA-VRP-3014) or the green fluorescent protein (GFP-VRP-3014 and GFP-VRP-3014) were prepared as previously described (MacDonald and Johnston, 2000 *J. Virology* 74:914). Briefly, RNA transcripts from replicon cDNA plasmids encoding the appropriate heterologous gene were co-electroporated with RNA transcripts from two helper constructs encoding either VEE capsid or VEE glycoprotein genes into baby hamster kidney (BHK) cells. VRP were harvested directly from the culture supernates 24 hr following electroporation and titered on BHK cells. For these studies, VRP were produced using a glycoprotein helper that contained the V3014 attenuating mutations in E1 272 (ala→thr) and E2 209 (glu→lys) (Davis et al., (1991) *Virology* 183:20).

Mice and Cells: Seven- to eight-week-old female CD1 out bred mice (Charles River Laboratory) were inoculated subcutaneously (sc) in the left rear foot pad with $5\times10^5$ infectious units (IU) of VEE viral replicon particles (VRP) unless otherwise specified. Mice were perfused with 4% paraformaldehyde (PFA) in PBS 24 hr post-inoculation (pi) and the draining popliteal lymph nodes were removed to PFA. Fixed frozen sections were analyzed by fluorescent microscopy for cells expressing GFP.

Bone marrow (BM) cells were isolated from the femurs of C57BL6 mice. Cells were grown as previously described. Briefly, marrow was flushed from femurs and tibia and resuspended in PBS. Cells were washed and re-suspended in RPMI1640 supplemented with 10% FBS, L-glutamine, non-essential amino acids, sodium pyruvate, 50 µM β-2-mercaptoethanol, 25 mM HEPES. Cultures were supplemented with 0.1 ng/ml GM-CSF alone or with either 5% conditioned culture medium from the epidermal fibroblast cell line, NS46 (Xu et al., (1995) *J. Immunol.* 154:2697) or 1 ng/ml IL-4 and grown on standard tissue culture plastic. The loosely adherent cells were removed to passage or to test for ADE by vigorous pipetting in the presence of 0.3 mM EDTA BHK and RAW 264 cells were grown according to American Tissue Type Culture. The Langerhans cell lines, XS106 and XS52 were cultured in RPMI1640 as described (Xu et al., (1995) J. Immunol. 154:2697). The B cell line, CH12LX (gift of S. Clarke) was grown in RPMI 1640 in 10% FBS and L-glutamine.

ADE assay: VRP were pre-incubated with antibodies for 30 min in PBS with 1% DCS on ice prior to infection of cells. $5 \times 10^5$ cells were infected with virus at a multiplicity of infection (MOI) of 1.0 in a 50 µl suspension for one hour at 37° C. after which the cells were plated in 24 well plates of low adhesion plastic (Low Cluster Plates; Costar). Cells were cultured for 18 hr. at which point cultures were fixed in 2% PFA and the frequency of GFP-positive cells was analyzed by FACS. To identify the mechanism responsible for ADE mediated infection, cells were first incubated with antibodies to either FcγRII/III, CR1 or an isotype control for 30 min on ice prior to infection with VRP.

Immunohistochemistry: Cells were incubated with the following antibodies to determine the cell surface phenotype: CD3, MHC class I, MHC class II, FcγRII/III, CR1, DEC 205, CD11c, CD11b and F4/80; and staining was analyzed by FACS. The cell types infected by VRP-3014 under different conditions were identified by double immunostaining of fresh frozen lymph node sections from mice 12 hours after sc footpad inoculations with HA-VRP-3014. Sections were fixed in acetone and incubated with chicken anti-influenza (kind gift of Mike Perdue) followed by a FITC-labeled anti-chicken secondary antibody. This was followed by incubation in cell-specific antibodies, including DEC 205, CD11c, CD11b and MHC class II and an appropriate rhodamine-labeled secondary antibody. Sections were analyzed for co-localized signal by confocal microscopy.

EXAMPLE 2

In Vitro Infection of Bone Marrow-Derived Dendritic Cells by VEE

An in vitro cell culture system for VEE infection was established and optimized following protocols used to grow dendritic cells from bone marrow. Cells grown by standard protocols for growing dendritic cells from bone marrow, i.e. in either GM-CSF alone (BM) or GM-CSF and IL4 (BM-IL-4) resulted in cells which were poorly permissive for VEE with only 0.1% of cells infected. When bone marrow cells were grown under the same conditions to establish Langerhans cell lines from skin (BM-NS; GM-CSF and conditioned media from an epidermal fibroblast cell line, NS47; Xu et al., (1995) J. Immunol. 154:2697) resulted in a ten to twenty-fold increase in specific infectivity by VEE. This is consistent with the previous observation that VEE preferentially infects Langerhans cells in vivo when given by a subcutaneous route of inoculation (MacDonald and Johnston, 2000 J. Virology 74:914). Analysis of cell surface markers demonstrated that cells grown under these conditions were negative for the T lymphocyte marker CD3 but shared dendritic cell (DEC 205 and CD11c) and macrophage (CD11b and F4/80) markers (FIG. 1). These cells were also positive for Fcγ receptor II/III and complement receptor I. Interestingly, while these cells were positive for MHC class I, they were negative for MHC class II, suggesting that these cells represent an early stage in dendritic cell differentiation.

EXAMPLE 3

Antibody to VEE Enhances Infection of BM-NS In Vitro

Figure 2A:
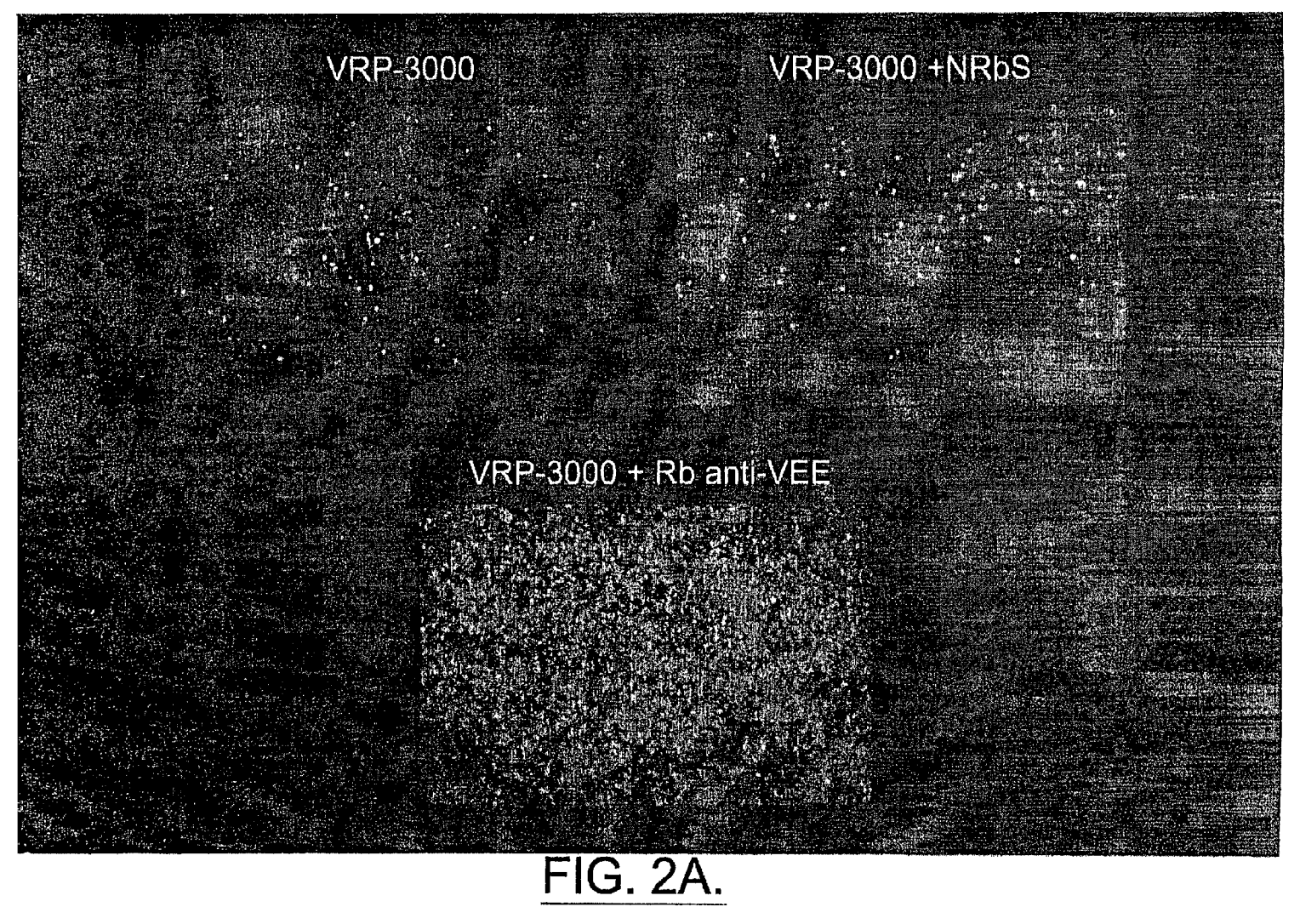
Figure 2B:
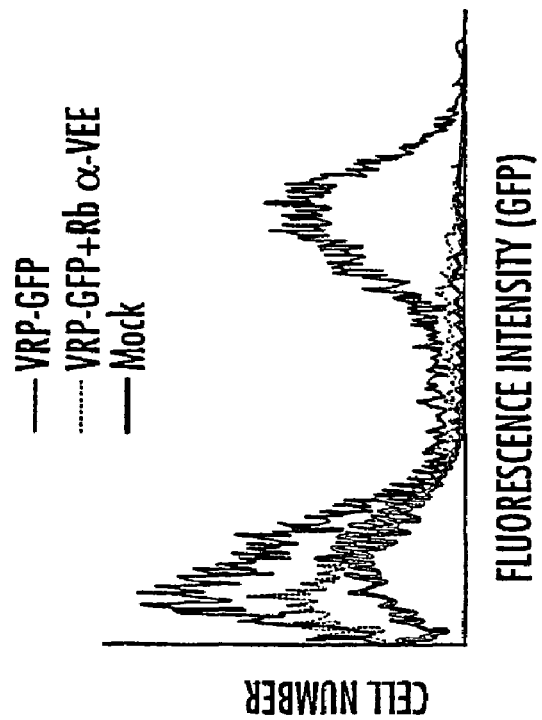
Figure 2B:
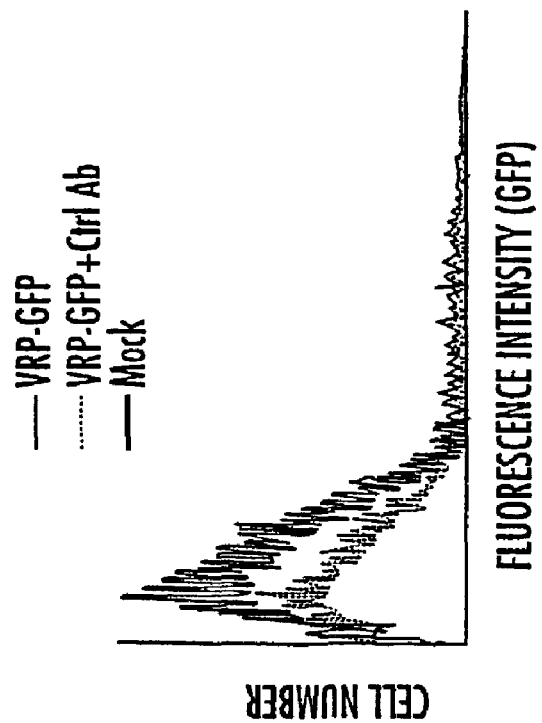
Figure 3:
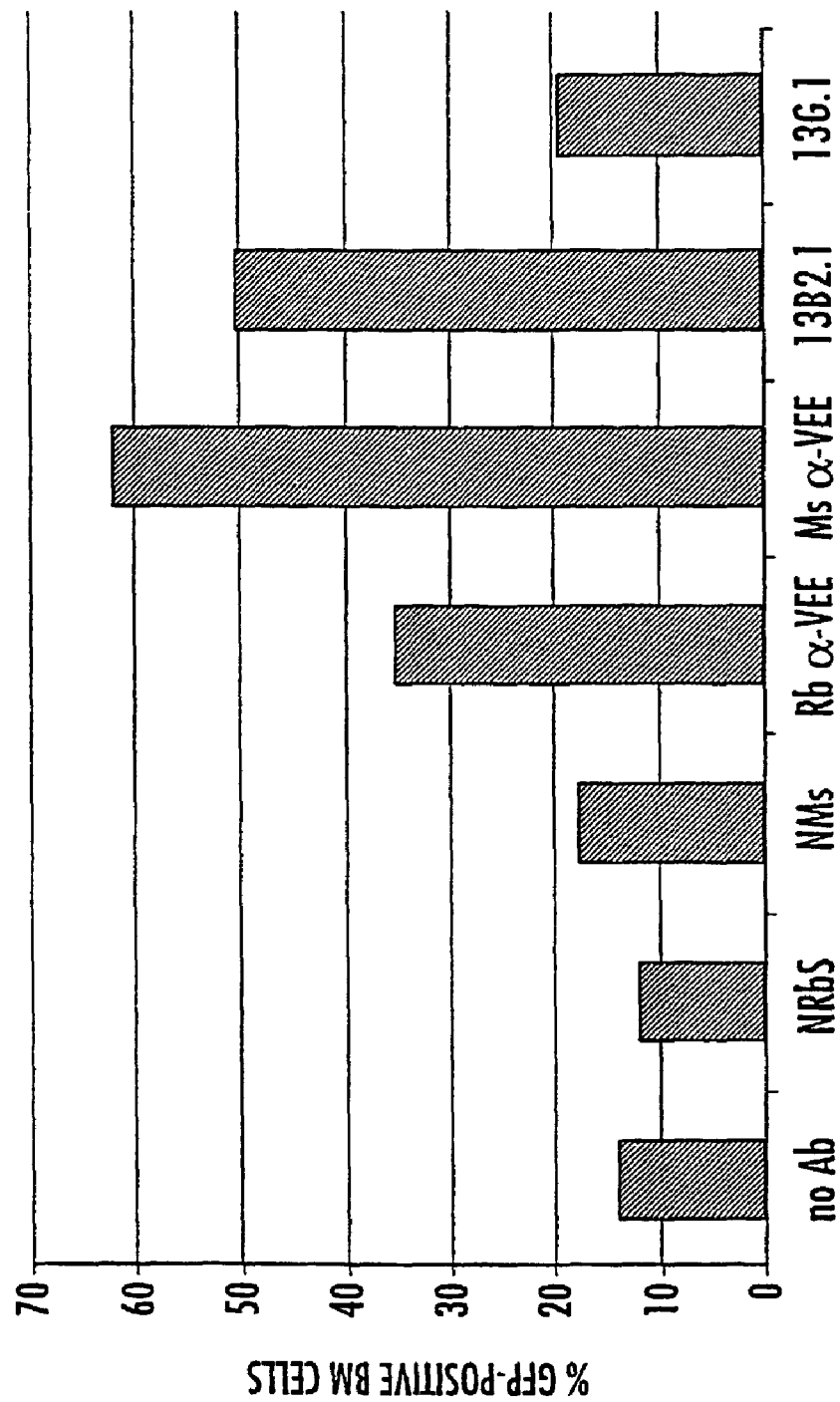
FIG. 3 is a graphical representation of ADE mediated by different VEE-specific antibodies. Percent of GFP-positive BM-NS cells as determined by FACS analysis 18 hr following either mock infection, infection with GFP-VRP-3000, or GFP-VRP-3000 at an MOI of 1.0 pre-incubated in normal rabbit serum (NRbS), normal mouse serum (NMS), rabbit anti-VEE serum (Rb α-VEE), mouse anti-VEE serum (Ms α-VEE), monoclonal VEE specific antibody, 13B2.1 or 13G.1.
Figure 6:
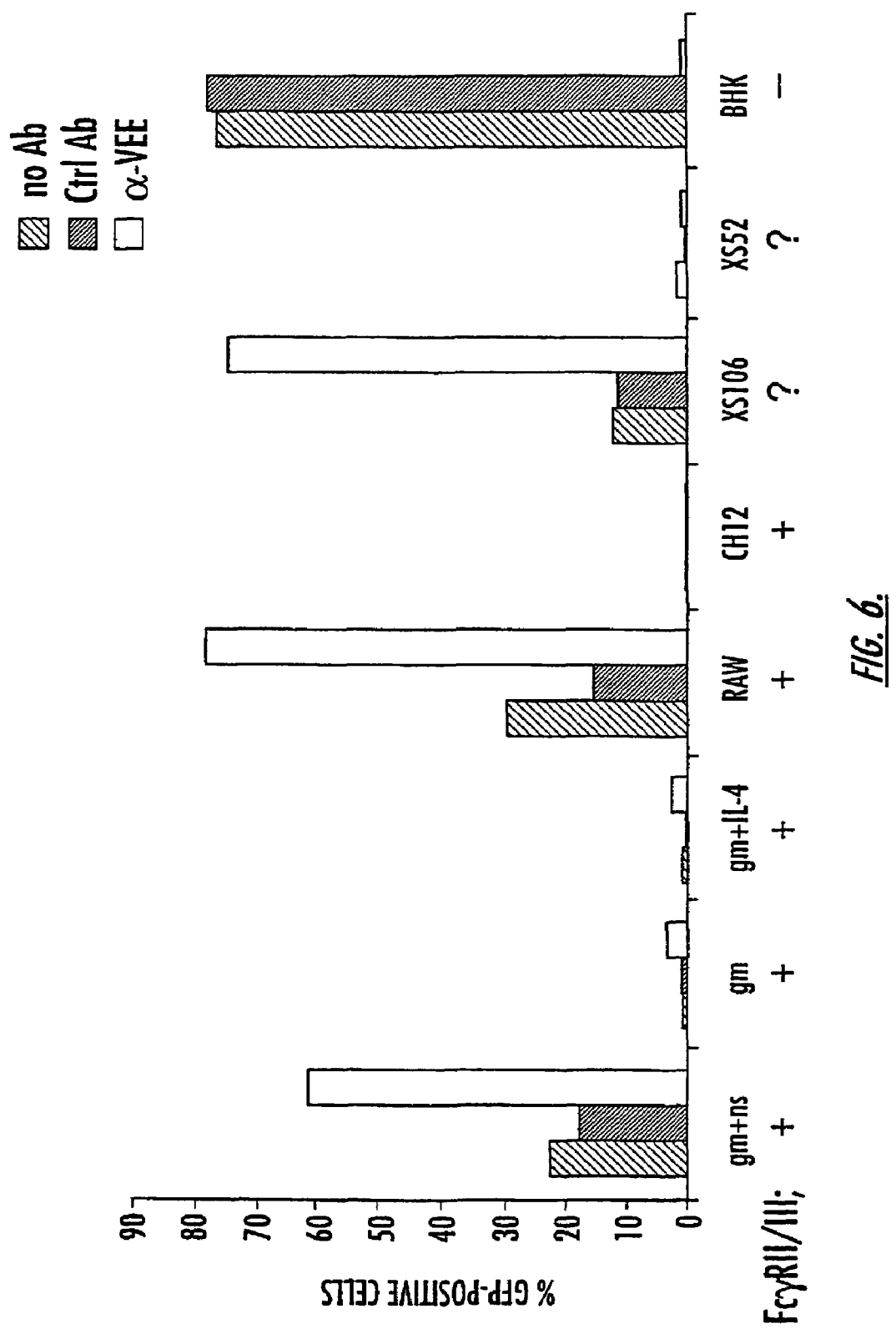
FIG. 6 demonstrates that FcγRII/III positive cells of myeloid lineages differ in susceptibility to ADE mediated VEE infection. Three different bone marrow preparations grown either in GM-CSF alone, GM-CSF and NS 46 conditioned media or GM-CSF and IL4, two Langerhans cell lines, XS106 and XS52, a macrophage cell line, RAW 264, a mature B cell line CH12LX, and Baby Hamster Kidney cells (BHK) were infected with GFP-VRP-3000 at an MOI of 1.0 either alone or pre-treated with control or VEE-specific antibodies. ADE was quantitated by FACS analysis of GFP-positive cell numbers.

Antibodies to Sindbis, a closely related alphavirus, have been shown to enhance infectivity of this virus on BHK cells independently of Fc receptors or complement (Flynn et al., (1988) Virology 166:82). Therefore, the potential enhancing activity of a rabbit anti-VEE antiserum previously shown to bind VEE infected cells (MacDonald and Johnston, 2000 J. Virology 74:914) was determined on BHK cells. In contrast to Sindbis, pre-treatment of VRP with VEE-specific antibodies diluted up to 1/6400 completely neutralized infection (FIG. 6). However, the same treatment of VRP with antibodies enhanced infection of BM-NS cells three to seven-fold (FIGS. 2A and 2B). Similar results were found using GFP-VRP coated in the VEE-3014 glycoprotein coat and incubating GFP-VRP-3014 in VEE3014 specific antibodies (data not shown). These same effects were observed with a polyclonal mouse anti-VEE serum and one of two monoclonal antibodies, 13B2.1, specific for VEE E1 glycoprotein (FIG. 3). ADE was not observed, however, with a second VEE E2-specific Mab, 13G.1.

EXAMPLE 4

FcγRII/III Expression is Necessary but not Sufficient for ADE

Figure 4:
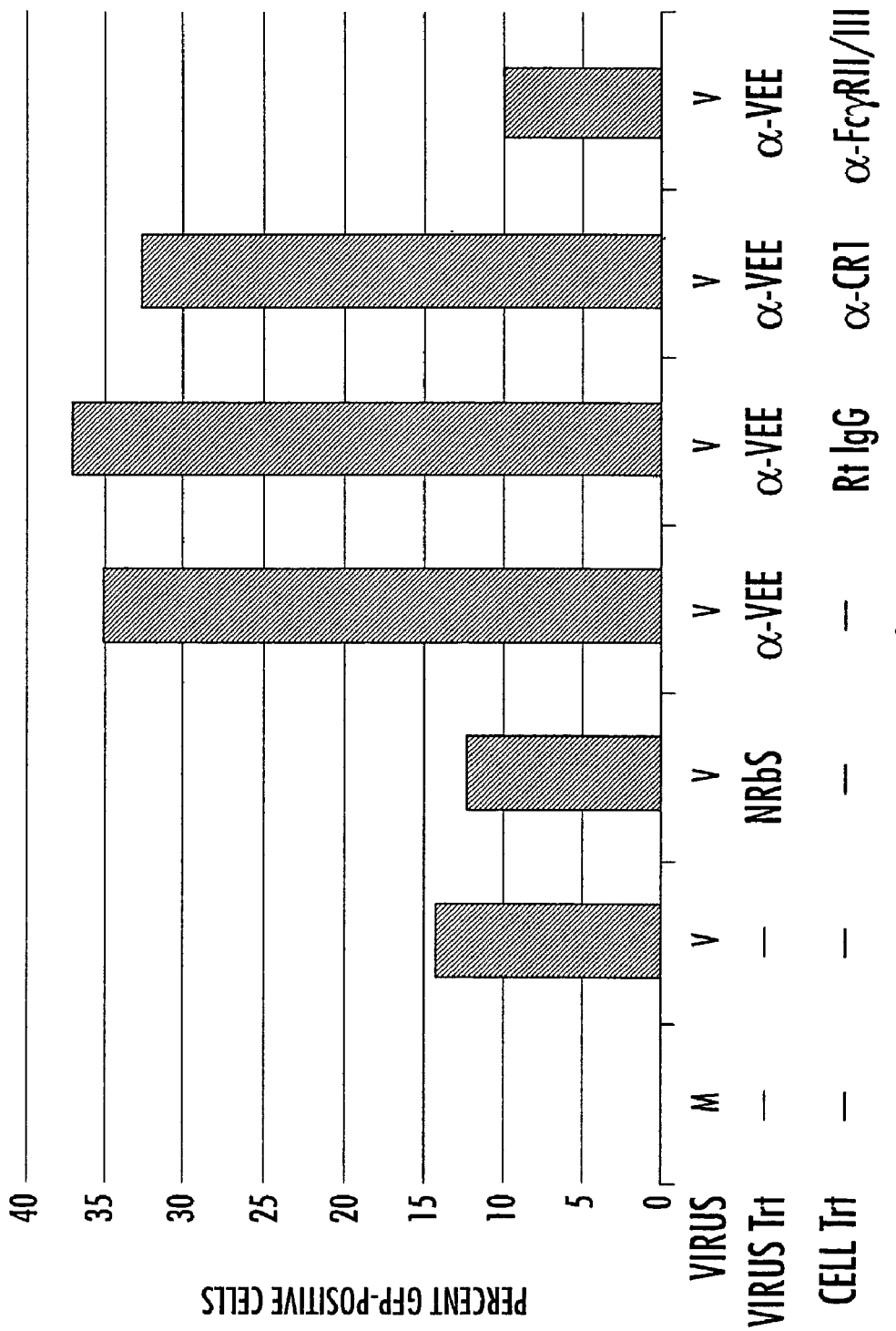
FIG. 4 demonstrates that FcγR/II/III blocks ADE in BM-NS cells. VRP pre-incubated in VEE-specific antibodies were mixed with BM-NS cells that were pre-treated with either diluent, an isotype matched negative control Mab, anti-CR1 Mab or anti-FcγRII/III Mab. ADE was quantitated by FACS analysis of GFP-positive cells.

To determine the mechanism responsible for ADE, serum was heat treated to inactivate complement. Heat treatment had no effect on the percent of GFP positive cells following antibody pre-treatment of VRP, suggesting a complement independent pathway. To further characterize the pathway, cells were pre-treated with antibodies to FcγRII/III, CR1, CR2 and CR3 (FIG. 4). Treatment which blocked Fcγ receptors reduced the level of infectivity to that of no antibody, indicating that ADE in this system is mediated primarily through FcγRII/III receptors. Anti-CR1 pre-treatment of cells had no effect on the level of ADE mediated infection.

EXAMPLE 5

FcγRII/III Positive Cells of Myeloid Lineages

Differ in Susceptibility to ADE Mediated VEE Infection

Figure 5:
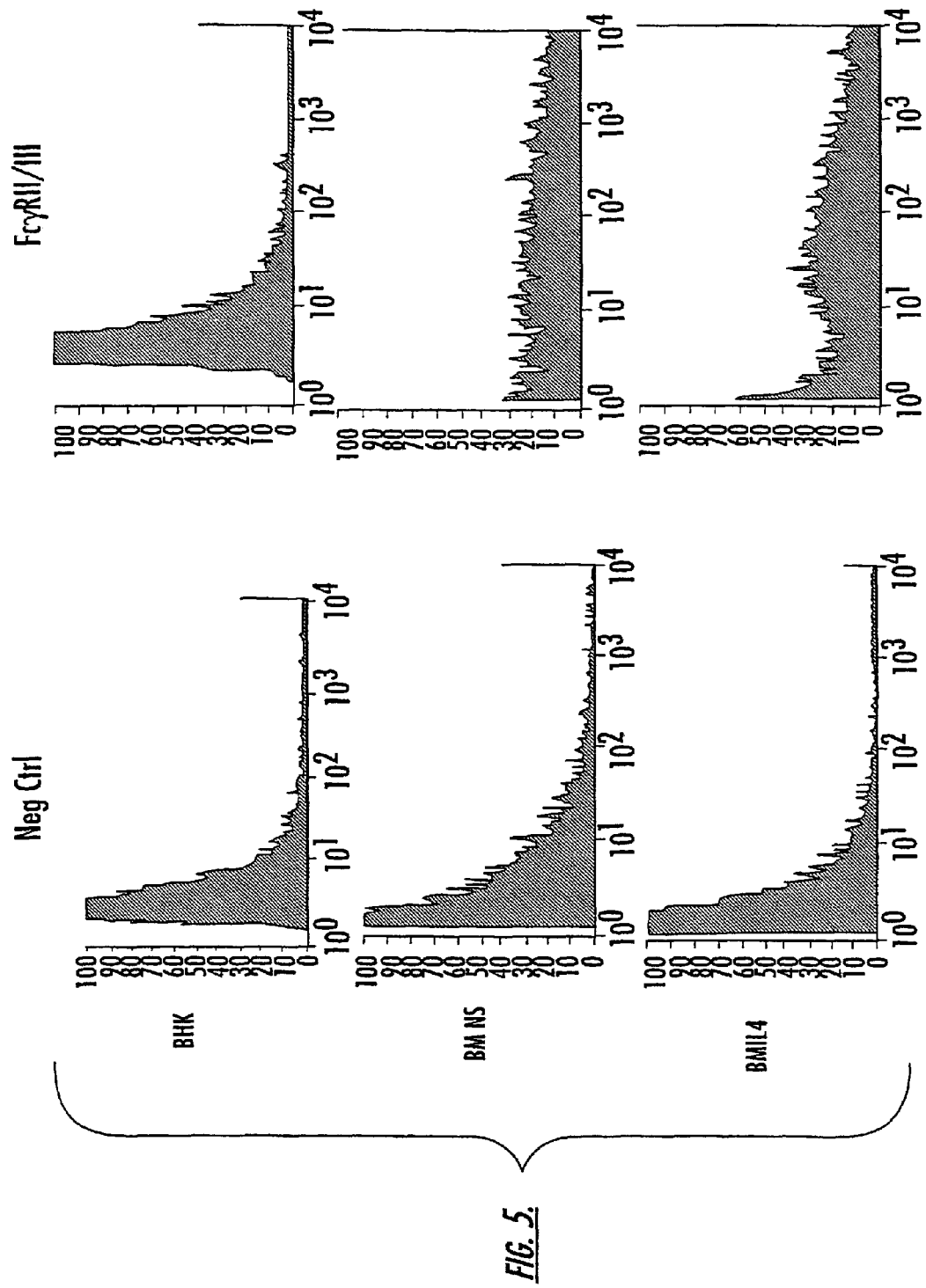
FIG. 5 presents data evaluating cell-surface expression of FcγRII/III. FACS analysis of FcγRII/III cell surface expression on BHK cells, on bone marrow cells grown either in GM-CSF alone (BM), GM-CSF and IL-4 (BM-IL-4) or GM-CSF and NS46 conditioned medium (BM-NS), two Langerhans cell lines, XS106 and XS 52, the macrophage cell line, RAW 264 and the B cell line, CH12.
Figure 5:
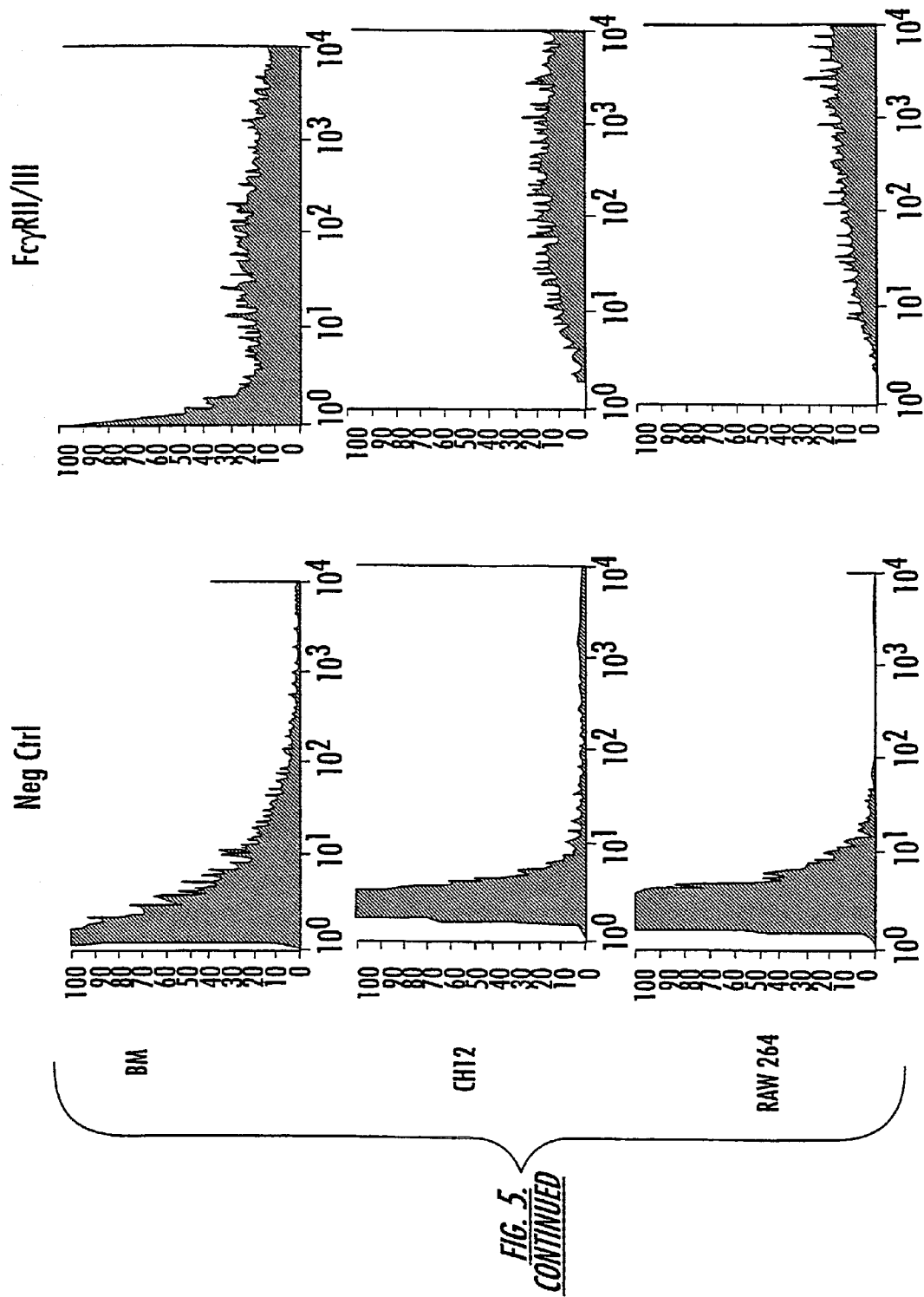

Dendritic cells from bone marrow grown under different conditions, GM-CSF alone (BM), GM-CSF and NS46 conditioned media (BM-NS) or GM-CSF and IL-4 (BM-IL-4), as well as cell lines of myeloid origin were screened for FcγRII/III expression. Those that were positive (FIG. 5) for Fcγ were tested for ADE mediated VRP infection (XS cells not yet characterized for Fcγ receptors). Not all cells that are positive for FcγR expression support ADE (FIG. 6). Interestingly, only BM-NS and not BM or BM-IL-4 were susceptible to ADE. In addition, antibody enhanced infection in the macrophage cell line, RAW 264 but not the in B cell line, CH12. Likewise only one of the two Langerhans cell lines, XS106 demonstrated ADE. These results indicate that FcγRII/III mediated uptake of the virus is not sufficient for productive viral infection, suggesting a block downstream of ADE mediated viral entry. In contrast, antibody to VEE neutralized infection on the VEE-permissive BHK cell line, cells that are negative for FcγR and complement receptors, illustrating the neutralizing capacity of these antibodies.

EXAMPLE 6

Antibody to VEE Alters Cell Targeting In Vivo

Figures 7A, 7B, 7C, 7D:
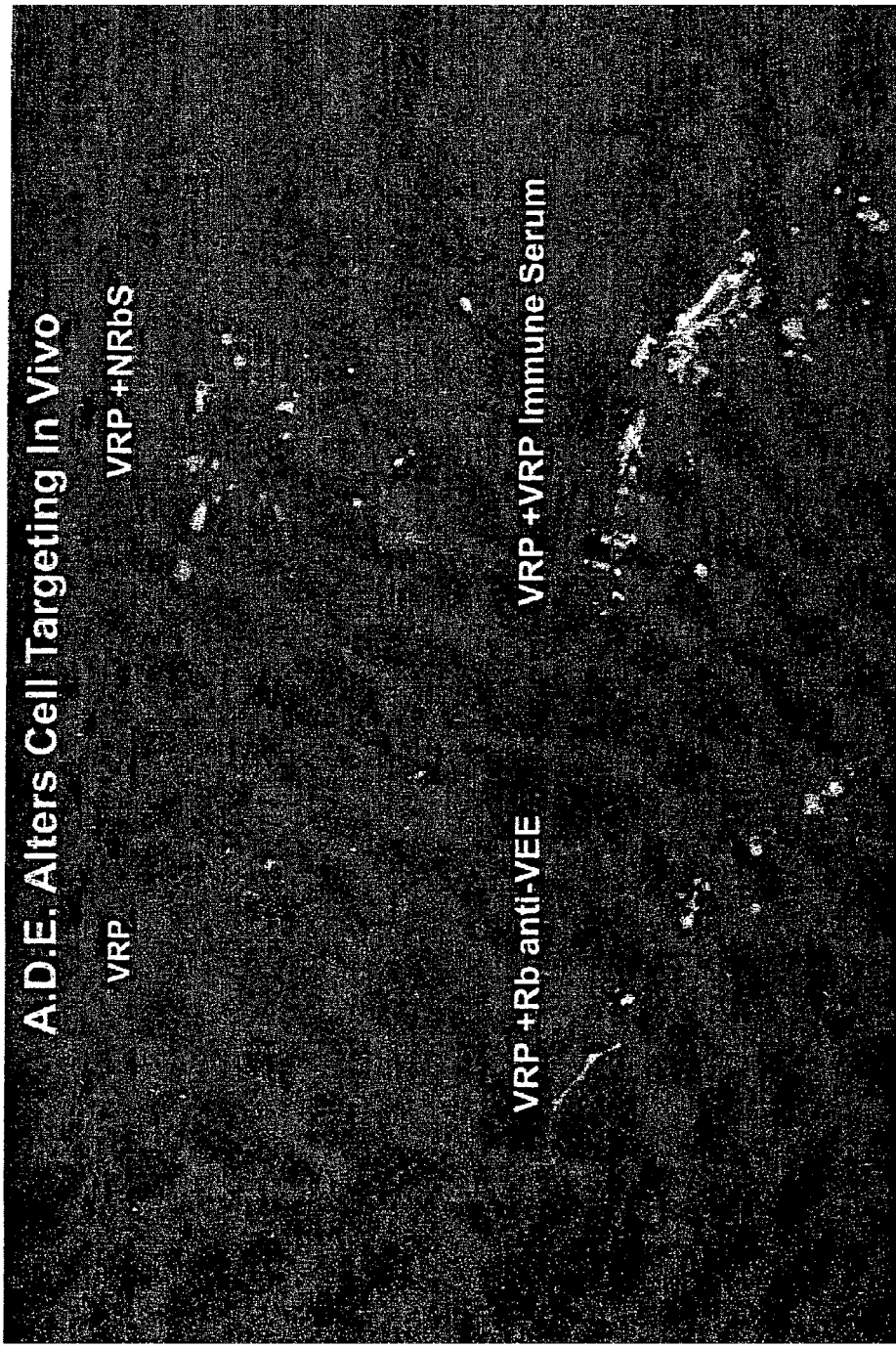
FIG. 7A-D presents photomicrographs demonstrating that ADE alters VRP cell targeting in vivo towards dendritic-like cells. Lymph node sections from mice twenty-four hours post-inoculation with GFP-VRP-3014 (A) alone or pre-incubated in either (B) normal rabbit serum, (C) rabbit anti-VEE antibodies, or (D) VRP immune serum.

To determine if antibody to VEE could affect cell targeting in vivo, mice were inoculated with VRP alone or VRP pre-incubated either in control serum or anti-VEE serum and the draining lymph nodes were examined for GFP-positive cells (FIGS. 7A-7D). A single dose of VRP packaged in the vaccine glycoprotein coat (3014) and at a dose used in vaccine protocols ($5 \times 10^5$ infectious units; IU) resulted in a limited number of predominantly small, round cells located mostly in the medulla, with occasional GFP-positive cells with dendritic cell morphology associated with B cell follicles (FIG. 7A). Pre-incubation of the VRP with a polyclonal VEE-specific antibody resulted in the appearance of a significant number of GFP-positive cells with Langerhans cell-like morphology just under the capsule, similar to what is seen with VRP packaged in wild type glycoproteins (FIG. 7C; MacDonald and Johnston, 2000 *J. Virology* 74:914). These results demonstrate that ADE can affect cell targeting in vivo.

Figures 8A, 8B, 8C:
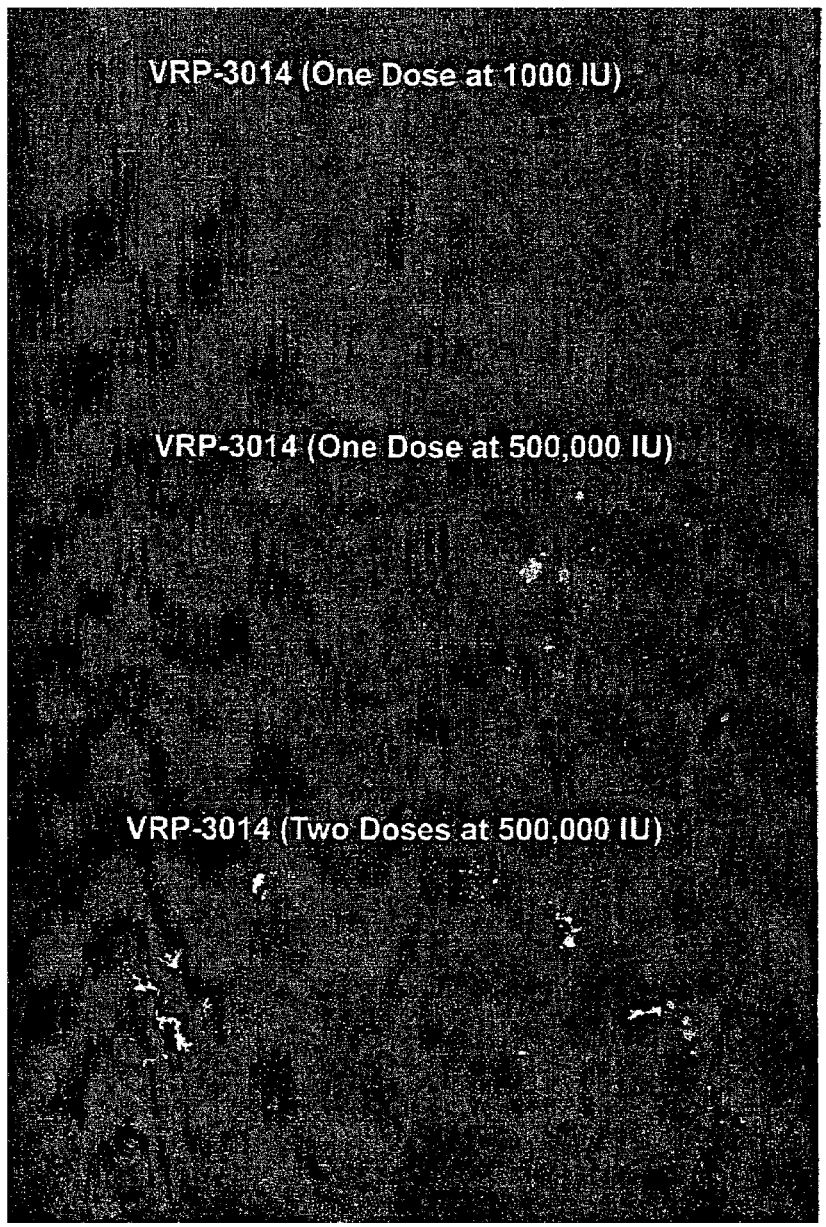
FIG. 8A-B provides photomicrographs demonstrating that VRP cell targeting is altered in VRP immune mice. Lymph node sections from mice twenty-four hours after either one dose of (A) $1\times10^3$ IU of GFP-VRP-3014, (B) $5\times10^5$ IU of GFP-VRP-3014, or (C) two doses of VRP; $5\times10^5$ IU of HA-VRP-3014 followed three weeks later with $5\times10^5$ IU of GFP-VRP-3014 pre-treated with VRP immune serum.

Vaccination of mice with VRP historically induces levels of VEE-specific antibodies that are undetectable by ELISA assays. Likewise prior immunity to VRP delivered heterologous antigens does not interfere with the generation of an immune response to subsequent VRP vaccines. These results suggest either that there is no antibody generated to the VRP themselves or that this antibody does not effectively neutralize the inoculated VRP. To test this, the effect of two sequential inoculations with VRP on cell targeting was determined. Mice that had been inoculated three weeks previously with VRP-3014 expressing influenza HA (HA-VRP-3014) or naïve mice were inoculated with a single dose of GFP-VRP-3014 and the GFP-positive cells in the draining lymph node were characterized (FIGS. 8A and 8B). Similar effects on cell targeting were found in lymph nodes of mice that had received two doses of VRP as was found in mouse inoculated with VRP pre-treated with VEE-specific antibodies. These results suggest that inoculation with a single dose of VRP results in the generation of anti-VRP antibodies that can significantly alter cell targeting towards Langerhans cell-like cells in an antibody dependent manner. To confirm this, mice were inoculated with VRP that were pre-treated with heat inactivated serum from mice three weeks after inoculation with HA-VRP-3014 (FIG. 8C). As with the previous two experiments, pre-treatment of the VRP with this serum resulted in a dramatic shift towards infection of dendritic cells as described above. These results demonstrate that antibody to VEE can significantly affect cell targeting in vivo.

Although the foregoing invention has been described in some detail by way of illustration and example for purposes of clarity and understanding, it will be obvious that certain changes and modifications may be practiced within the scope of the appended claims and equivalents thereof.

That which is claimed is:

1. A method of administering a nucleotide sequence to a subject, comprising:
    (a) administering a Venezuelan Equine Encephalitis (VEE) vector comprising a heterologous nucleotide sequence to a subject; and
    (b) administering an antibody that specifically binds to the E1 glycoprotein and/or the E2 glycoprotein of the VEE vector to the subject;
    wherein said administering steps of (a) and (b) are concurrent;
    whereby the heterologous nucleotide sequence is introduced into and expressed in the subject.

2. The method of claim 1, wherein there is no significant pathology in the subject as a result of said administering steps.

3. The method of claim 1, wherein the subject is selected from the group consisting of primate, bovine, ovine, caprine, porcine, equine, feline, canine, lagomorph, and rodent subjects.

4. The method of claim 3, wherein the subject is a human subject.

5. The method of claim 1, wherein the VEE vector and the antibody are administered in a single formulation.

6. A method of administering a nucleotide sequence to a subject, comprising:
    (a) administering a Venezuelan Equine Encephalitis (VEE) vector comprising a heterologous nucleotide sequence to a subject; and
    (b) administering an antibody that specifically binds to the E1 glycoprotein and/or the E2 glycoprotein of the VEE vector to the subject;
    wherein the antibody is administered prior to the VEE vector;
    whereby the heterologous nucleotide sequence is introduced into and expressed in the subject.

7. The method of claim 6, wherein there is no significant pathology in the subject as a result of said administering steps.

8. The method of claim 6, wherein the subject is selected from the group consisting of primate, bovine, ovine, caprine, porcine, equine, feline, canine, lagomorph, and rodent subjects.

9. The method of claim 8, wherein the subject is a human subject.

* * * * *

UNITED STATES PATENT AND TRADEMARK OFFICE
CERTIFICATE OF CORRECTION

PATENT NO. : 7,651,998 B1  Page 1 of 1
APPLICATION NO. : 10/069305
DATED : January 26, 2010
INVENTOR(S) : MacDonald et al.

It is certified that error appears in the above-identified patent and that said Letters Patent is hereby corrected as shown below:

Column 3, Line 51, Brief Description of the Drawings: Please correct "FIG. 8A-8B" to read -- FIG. 8A-8C --

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,651,998 B1 | Page 1 of 1 |
| APPLICATION NO. | : 10/069305 | |
| DATED | : January 26, 2010 | |
| INVENTOR(S) | : MacDonald et al. | |

It is certified that error appears in the above-identified patent and that said Letters Patent is hereby corrected as shown below:

On the cover page, (*) Notice: Subject to any disclaimer, the term of this patent is extended or adjusted under 35 USC 154(b) by 600 days.

Delete the phrase "by 600 days" and insert --by 1089 days--

Signed and Sealed this

Twenty-second Day of June, 2010

David J. Kappos
*Director of the United States Patent and Trademark Office*